(12) United States Patent
Moon et al.

(10) Patent No.: US 8,216,595 B2
(45) Date of Patent: Jul. 10, 2012

(54) POWERFUL VACCINE COMPOSITION COMPRISING LIPOPEPTIDE AND POLY I:C AS AN ADJUVANT

(75) Inventors: Hong Mo Moon, Englewood Cliffs, NJ (US); Byung Cheol Ahn, Gyeonggi-do (KR); Jung-Sun Yum, Gyeonggi-do (KR)

(73) Assignee: Dobeel Corporation, Seongnam-si (KR)

(*) Notice: Subject to any disclaimer, the term of this patent is extended or adjusted under 35 U.S.C. 154(b) by 311 days.

(21) Appl. No.: 12/314,162

(22) Filed: Dec. 5, 2008

(65) Prior Publication Data

US 2009/0155308 A1 Jun. 18, 2009

(30) Foreign Application Priority Data

Dec. 7, 2007 (KR) .................. 10-2007-0126775

(51) Int. Cl.
*A61K 47/00* (2006.01)
*A61K 39/00* (2006.01)
(52) U.S. Cl. .................. 424/283.1; 424/184.1
(58) Field of Classification Search .................. None
See application file for complete search history.

(56) References Cited

U.S. PATENT DOCUMENTS

2003/0157135 A1* 8/2003 Tsuji et al. .................. 424/278.1

FOREIGN PATENT DOCUMENTS

KR 10-0836745 B1 6/2008

OTHER PUBLICATIONS

Steenbergen et al., Journal of Antimicrobial Chemotherapty, 2005, 55:283-288.*
Rharbaoui et al., European Journal of Immunology, 2002, 32(10):2857-2865.*
Ichinohe et al., Journal of Virology, 2005, 79(5):2910-2919.*
Bessler et al., International Immunopharmacology, 2003, 3:1217-1224.*
Avramidis et al., Veterinary Microbiology 2002, 88:325-338.*
Erdile et al., Vaccine, 1997, 15(9):988-996.*
Zeng et al., J. Immunol., 2002, 169:4905-4912.*
Dempsey, Paul W. et al., "C3d of Complement as a Molecular Adjuvant: Bridging Innate and Acquired Immunity", Science, 1996, pp. 348-350, vol. 271.
Deres, Karl et al., "In vivo priming of virus-specific cytotoxic T lymphocytes with synthetic lipopeptide vaccine", Nature, 1989, pp. 561-564, vol. 342.
Gavin, Amanda L., "Adjuvant-Enhanced Antibody Responses in the Absence of Toll-Like Receptor Signaling", Science, 2006, pp. 1936-1938, vol. 314.
Yoder, Alyson et al., "Tripalmitoyl-S-Glyceryl-Cysteine-Dependent OspA Vaccination of Toll-Like Receptor 2-Deficient Mice Results in Effective Protection from Borrelia burgdorferi Challenge", Infection and Immunity, 2003, pp. 3894-3900, vol. 71, No. 7, American Society for Microbiology.
Nimmerjahn, Falk et al., "Divergent Immunoglobulin G Subclass Activity Through Selective Fc Receptor Binding", Science, 2005, pp. 1510-1512, vol. 310.
Coutelier, Jean-Paul et al., "IgG2a Restriction of Murine Antibodies Elicited by Viral Infections", J. Exp. Med., 1987, pp. 64-69, vol. 165, the Rockefeller University Press.
Markine-Goriaynoff, Dominique et al., "Increased Efficacy of the Immunoglobulin G2a Subclass in Antibody-Mediated Protection against Lactate Dehydrogenase-Elevating Virus-Induced Polioencephalomyelitis Revealed with Switch Mutants", Journal of Virology, 2002, pp. 432-435, vol. 76, No. 1, American Society for Microbiology.
Bagchi, Aranya et al., "MyD88-Dependent and MyD88-Independent Pathways in Synergy, Priming, and Tolerance between TLR Agonists", The Journal of Immunology, 2007, pp. 1164-1171, vol. 178, The American Association of Immunologists, Inc.
Metzger, Jörg et al., "Synthesis of novel immunologically active tripalmitoyl-S-glycerylcysteinyl lipopeptides as useful intermediates for immunogen preparations", Int. J. Peptide Protein Res., 1991, pp. 46-57, vol. 37.
Schild, Hansjörg et al., "Efficiency of peptides and lipopeptides for in vivo priming of virus-specific cytotoxic T cells", Eur. J. Immunol., 1991, pp. 2649-2654, vol. 21, VCH Verlagsgesellschaft mbH, Weinheim, Germany.
Trinchieri, Giorgio et al., "Cooperation of Toll-like receptor signals in innate immune defence", Immunology, 2007, pp. 179-190, vol. 7, Nature Publishing Group.
Magee, Wayne E. et al., "The Liver as a Site for Interferon Production in Response to Poly I:Poly C", Life Sciences, 1972, pp. 1081-1086, vol. 11, Part II, Pergamon Press, Great Britain.
Manetti, Roberto et al., "Polyinosinic acid: polycytidylic acid promotes T helper type 1-specific immune responses by stimulating macrophage production of interferon-α and interleukin-12", Eur. J. Immunol., 1995, pp. 2656-2660, vol. 25, VCH Verlagsgesellschaft mbH, Weinheim, Germany.
Rouas, Redouane et al., "Poly(I:C) used for human dendritic cell maturation preserves their ability to secondarily secrete bioactive IL-12", International Immunology, 2004, pp. 767-773, vol. 16, No. 5, the Japanese Society for Immunology.
Cui, Zhengrong et al., "Synthetic double-stranded RNA poly(I:C) as a potent peptide vaccine adjuvant: therapeutic activity against human cervical cancer in a rodent model", Cancer Immunol. Immunother., 2006, pp. 1267-1279, vol. 55, Springer-Verlag.
Miller, Glenn A. et al., "The identification of clinically relevant markers and therapeutic targets", Drug Discovery Today, 2003, pp. 31-38, vol. 8, No. 1, Elsevier Science Ltd.
Kawakami, Yutaka et al., "Human Tumor Antigens Recognized by T-Cells", Immunologic Research, 1997, pp. 313-339, vol. 16, No. 4, Humana Press Inc.
Slingluff Jr, Craig L. et al., "Direct analysis of tumor-associated peptide antigens", Current Opinion in immunology, 1994, pp. 733-740, vol. 6, Current Biology Ltd.

* cited by examiner

Primary Examiner — Zachariah Lucas
Assistant Examiner — Nicole Kinsey White
(74) Attorney, Agent, or Firm — Vorys, Sater, Seymour and Pease LLP; Mih Suhn Koh

(57) ABSTRACT

The present invention relates to an adjuvant comprising a lipopeptide and poly I:C. When the adjuvant of the present invention is used, the level of antigen specific antibody induction is synergistically increased and Th1 type immune response is also induced. Therefore, the adjuvant of the present invention can be very effectively used as an adjuvant in the formulation of preventive and therapeutic vaccines for viral or parasitic infection and cancer.

19 Claims, 10 Drawing Sheets

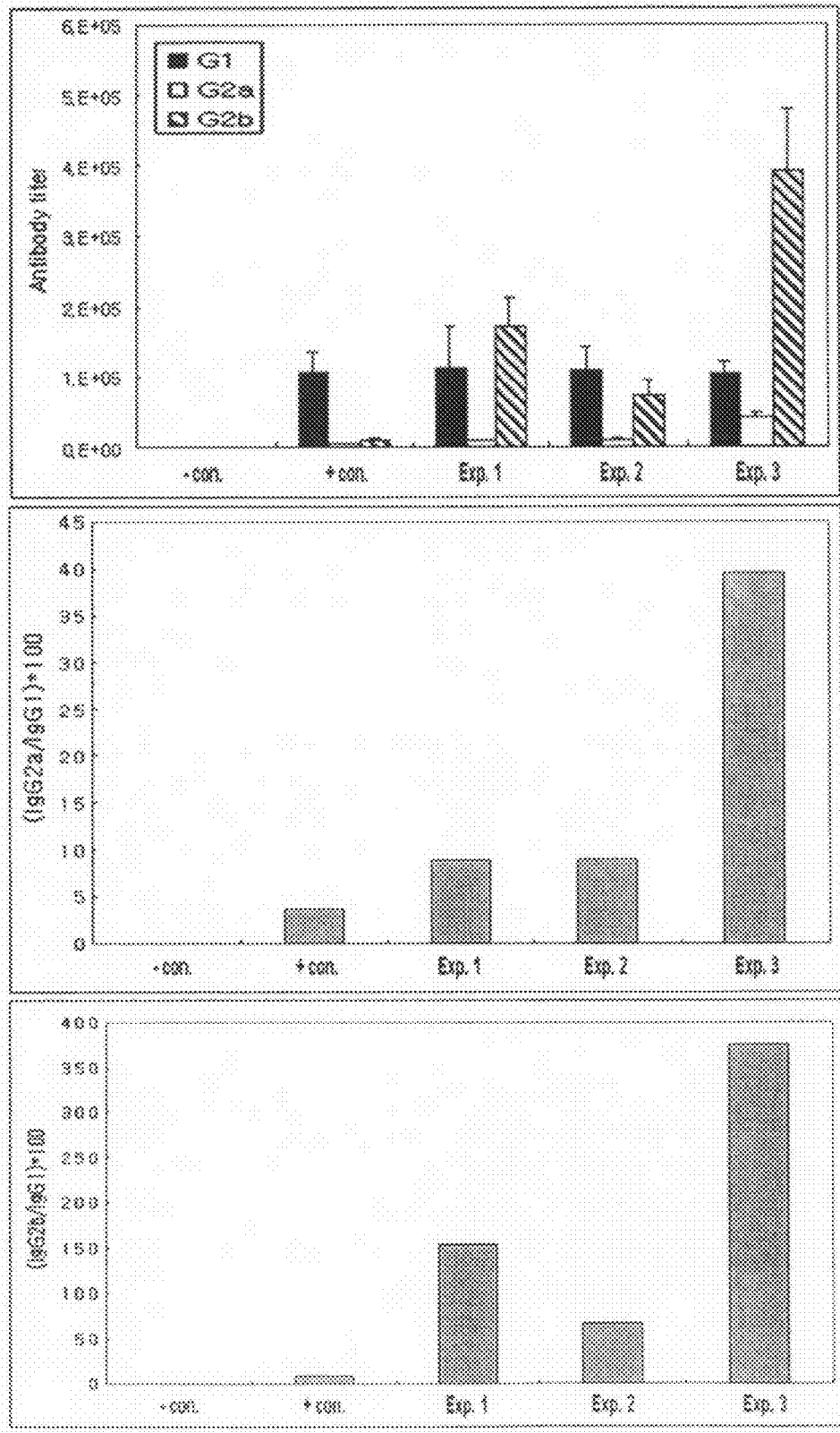

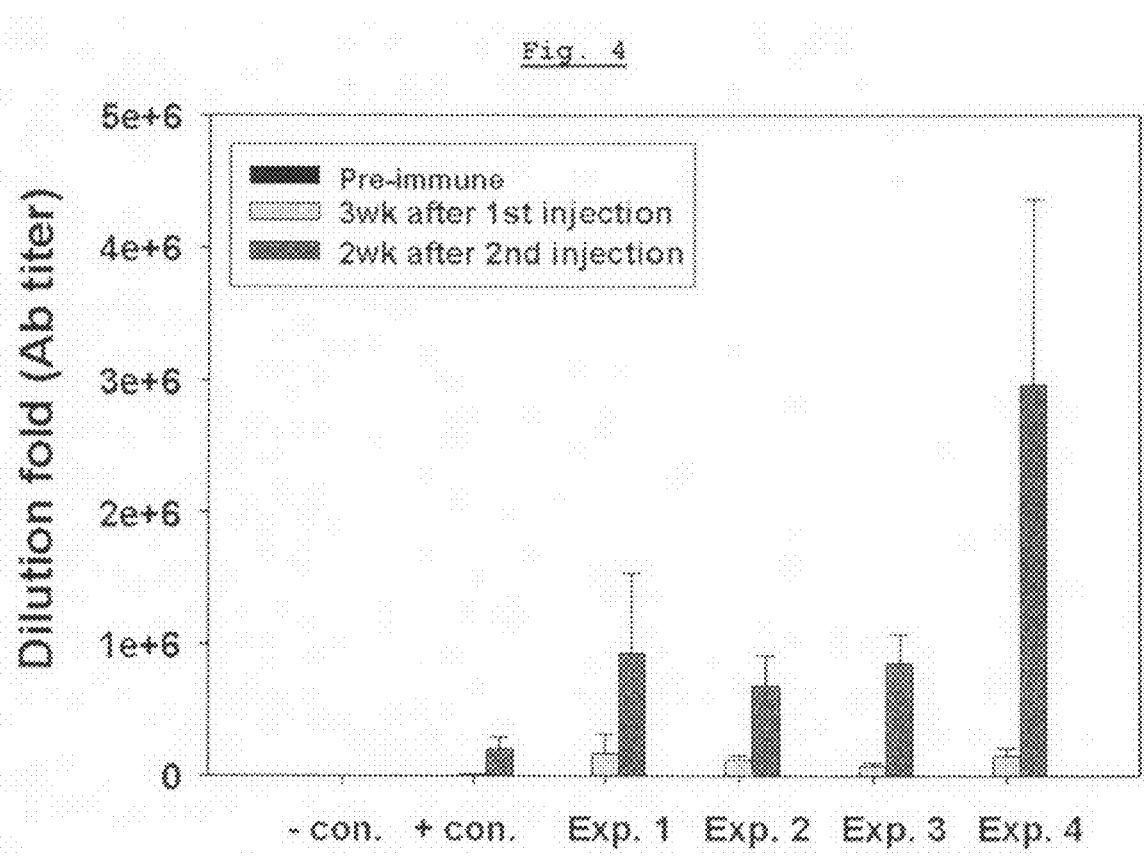

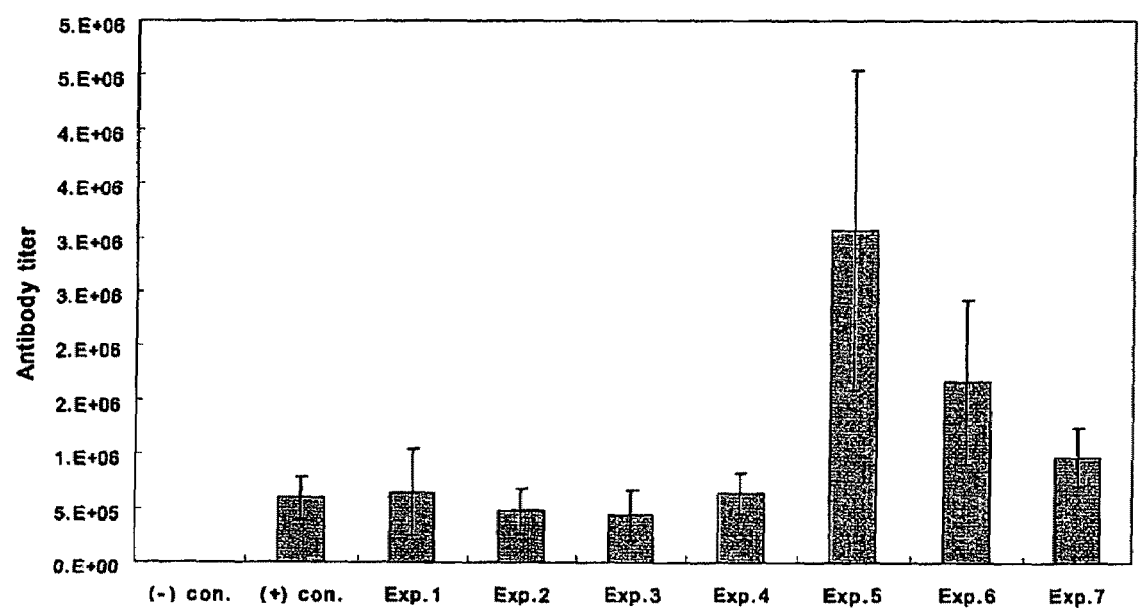

POWERFUL VACCINE COMPOSITION COMPRISING LIPOPEPTIDE AND POLY I:C AS AN ADJUVANT

FIELD OF THE INVENTION

The present invention relates to an adjuvant. In particular, the present invention relates to an immune-stimulating adjuvant having a synergistic effect in inducing immune responses comprising one or more lipopeptide(s) and poly I:C (polyinosinic:polycytidylic acid). Further, the present invention relates to a vaccine composition comprising said adjuvant and an antigen, and to a method for treatment and/or prevention of a viral or parasite infection or a cancer using the same.

BACKGROUND OF THE INVENTION

An adjuvant plays a role in promoting immune responses by accelerating or amplifying one or more specific phases of various immune responses. When an adjuvant is co-administered with an antigen, it can improve immunogenicity of the antigen and/or alter the type of immune response against the antigen. Typical examples of such adjuvants are an oil emulsion (Freund's adjuvant), monophosphoryl lipid A (MPL), Q saponins, aluminum hydroxide or phosphate or calcium salts (alum) of aluminum, non-ionic block polymer surfactants, lipopolysaccharides, mycobacteria, tetanus toxoid, CpG, etc.

Using a protein antigen alone does not often induce a sufficiently strong and a desired type of immune response, so vaccine compositions normally contain an antigen in combination with an adjuvant. According to a two signal model for the immune response, one signal delivered through the engagement of the antigen epitope presented with MHC molecule and antigen receptor is not enough to induce the immune response. It requires additional signals generated from co-stimulatory molecule(s). In this regard, the adjuvant may be able to enforce the signal strength generated by co-stimulatory molecules through induction of co-stimulatory molecules such as CD 40, CD 80, and CD 86 on antigen presenting cell (DC). It also induces MHC molecules and cytokines that determine the type of the immune response.

Some antigens such as lipoproteins, glycoproteins, or whole microorganisms can act both as an epitope and an adjuvant in the form of a pathogen associated molecular pattern (PAMP). The primary structure of a protein antigen, namely the amino acid sequence of an antigen, cannot be changed, but the PAMP of an antigen can be modified or supplemented by the addition of a proper adjuvant or subsidiary structure to affect immunogenicity (Dempsey P W et al., Science 271: 348-350, 1996; Deres K et al., Nature 342: 561-564, 1989).

The modification of a molecular pattern of an antigen can increase immunogenicity and also affect the type of elicited immune response. For example, in the case of an HBV surface antigen, S-protein without preS1 and preS2 does not exhibit immunogenicity in certain congenic mouse strains, while L-protein containing preS1 and preS2 not only induces the generation of antibody against preS1 and preS2 but also helps to induce the generation of antibody against S antigen (Milich D R et al., 1986, *New Approaches to Immunization*, pp 377-382. Cold Spring Harbor Laboratories, New York).

When a whole pathogenic microorganism is used as an antigen, it is expected that the microorganism contains various types of PAMP, such as lipopolysaccharides, nucleic acids, lipoproteins and conjugated proteins. In this case, the pathogen recognition receptor (PRR) existing on the surface of antigen presenting cell (APC) recognizes the PAMP to generate signals inducing various co-stimulatory molecules and cytokines, which affects the type of immune response as well as the level thereof. For example, interferon gamma and IL-12 helps to induce Th1 (T helper cell 1) response which plays an important role in immune response against virus infection. Th1 type immune response leads to the increase of IgG2a and IgG2b generation and induces a powerful cell mediated immune response. In this case, antigen associated various types of PAMPs act as an adjuvant and such adjuvant can help the regulation of immune responses.

A lipopeptide was first synthesized by Metzger et al. as a synthetic analogue of lipopeptide originated from bacteria and mycoplasma (Metzger J et al., *Int J Peptide Protein Res* 37:46-57, 1991). Since then, numerous analogues have been synthesized (EMC microcollections GmbH Sindelfinger Str. 3 72070 Tubingen, Germany). There is a report that virus-specific cytotoxic T lymphocyte (CTL) was induced by administrating a mouse with Pam3Cys-Ser-Ser, a lipopeptide conjugated with influenza virus T cell epitope (Schild H et al., *Eur J Immunol* 21:2649-2654, 1991). In general, the lipopeptide has been known as a TLR 2 ligand (Trinchieri G & Sher A, *Nat Rev Immunol* 7:179-190, 2007).

Poly I:C has been used as a powerful inducer of type I interferon in in vitro and in vivo studies (Magee M E & Griffith M J, *life Science* II, 11:1081-1086, 1972; Manetti Y R et al., *Eur. J. Immunol.* 25:2656-2660, 1995), and has been known to induce dendritic cell (DC) maturation, the most popular antigen presenting cell (APC) in mammals. The matured DC is capable of inducing immune response effectively (Rous R et al., *International Immunol* 16:767-773, 2004). Poly I:C is also known as an IL-12 inducer, and the IL-12 is an important cytokine, inducing cell mediated immune response and IgG2a antibody generation by promoting the enhancement of Th1 development. Adjuvant activity of poly I:C was also previously known (Cui Z & Qui F, *Cancer Immunol Immunotherapy* 16:1-13, 2005).

These types of natural adjuvants associated with the antigens, however, often may not be strong enough to induce a desired strength and a quality of immune response, requiring a good adjuvant in a vaccine formulation.

Developing a good adjuvant is accordingly a very important job in developing a good vaccine, but adjuvant development still has to rely mainly on empirical work. For example, Toll Like Receptors (TLR) are the most important PRR on antigen presenting cells (APC) involved in the activation of APC and in antigen presentation by APC. Potent antibody response, however, is not entirely dependent on TLR signals (Gavin. A. L. et al, *Science* 314:1936-1938, 2006). Further, Pam3cys, which is a TLR2 ligand, works in inducing immune response independently of TLR2 (Yoder et al, *Infect. Immun.* 71:3894-3900, 2003). Accordingly, although Pam3Cys and poly I:C are known to be synergistic in inducing TNF-α and IL-6 in macrophages (Bagchi et al, *J. Immun.* 178:1164-1171, 2007), no teaching of a well balanced powerful adjuvant function of a similar combination consisting of a lipopeptide and poly I:C is found in the prior art. To make matters further complicated, good protective immune response requires balanced immune response comprising both strong cell mediated immune response and humoral antibody response. Therefore, developing an adjuvant that will help to induce well balanced adaptive immune response still can not be rationally predicted.

BRIEF SUMMARY OF THE INVENTION

The present inventors have achieved the present invention by finding and confirming that an adjuvant composition comprising a lipopeptide and poly I:C (polyinosinic:polycytidylic acid) is far more powerful than the conventional adjuvant, aluminum hydroxide. Further, the present inventors have confirmed that the mixture of one or more lipopeptide(s) and poly I:C as an adjuvant is synergistic, instead of additive, in stimulating adaptive immune responses. Such a well balanced powerful adjuvant comprising a mixture of a lipopeptide and poly I:C as described above was an unexpected finding. The present inventors further confirmed that a covalent linking of a lipopeptide to an antigen was not required in the present invention. A simple formulation in the form of a mixture of a lipopeptide, poly I:C, and at least one antigen was sufficient to achieve the well balanced powerful adjuvant according to the present invention.

Accordingly, it is an object of the present invention to provide an immune-stimulating adjuvant that can help an antigen induce a strong immune response.

It is another object of the present invention to provide an adjuvant composition that can be used in a vaccine formulation to induce a strong humoral immune response and cell mediated immune response.

It is another object of the present invention to provide a method for generating an appropriate, high quality antibody using said adjuvant composition.

It is another object of the present invention to provide a method for enhancing a Th1 immune response using said adjuvant composition.

It is another object of the present invention to provide an adjuvant composition to prepare a therapeutic vaccine for viral or parasite infection, containing said adjuvant composition and at least one viral or parasite antigen.

It is another object of the present invention to provide an adjuvant composition to prepare a preventive or therapeutic vaccine against cancer, containing said adjuvant composition and at least one cancer-specific antigen.

To achieve these objects, the present invention, in one aspect, provides an immune-stimulating adjuvant comprising one or more lipopeptide(s) and poly I:C (polyinosinic:polycytidylic acid) wherein the lipopeptide and poly I:C synergistically stimulate the immune responses. The lipopeptide may include, but is not limited to, Pam3Cys-SKKKK, Pam3Cys-SR8, FLS-1, PHC-SKKKK, Ole2 PamCys-SKKKK, Pam2Cys-SKKKK, PamCys(Pam)-SKKKK, Ole2Cys-SKKKK, Myr2Cys-SKKKK, PamDhc-SKKKK, PamCSKKKK, Dhc-SKKKK and mixtures thereof. The poly I:C is preferably about 50-2,000 bp in length.

In another aspect, the present invention provides a vaccine composition containing said adjuvant and at least one appropriate antigen. The antigen may include, but is not limited to, a protein of a pathogen, a recombinant protein, a peptide, a hapten, a polysaccharide, a glycoprotein, a lipopolysaccharide, a DNA molecule (polynucleotide), a cancer cell, a micro-organism, and mixtures thereof. Preferably, the antigen may include L-HBsAg, influenza HA, S-protein and preS. The vaccine composition according to the present invention can efficiently induce the cell mediated immune response and produce appropriate antigen-specific high quality antibodies, preferably IgG1, IgG2a and IgG2b type antibodies.

In another aspect, the present invention provides a pharmaceutical composition comprising said adjuvant and at least one active ingredient. The pharmaceutical composition may further comprise at least one ingredient selected from the group consisting of pharmaceutically acceptable carriers, pharmaceutically acceptable additives and adjuvants.

In another aspect, the present invention provides a method for generating an appropriate, high quality antibody comprising administrating the adjuvant composition and an antigen to a subject in need thereof. In another aspect, the present invention provides a method for enhancing Th1 immune response comprising administrating the vaccine composition to a subject in need thereof.

In another aspect, the present invention provides a method to treat a viral or parasite infection, comprising administrating the adjuvant composition and at least one viral or parasite antigen. The viral antigen includes, but is not limited to, influenza virus antigen (HA: haemagglutinin or neuraminidase antigen), human papilloma virus (HPV) antigen, human immunodeficiency virus (HIV) antigen (GP-120, GP-160), vesicular stomatitis virus antigen (vesicular stomatitis virus glycoprotein), cytomegalovirus (CMV) antigen, hepatitis antigen [hepatitis A(HAV), B(HBV), C(HCV), D(HDV) and G(HGV): L-HBsAg, S-HBsAg, M-HBsAg, pre S], respiratory syncytial virus (RSV) antigen and herpes simplex virus antigen. The parasite includes, but is not limited to, protozoa, nematoda, trematoda and cestoda.

In another aspect, the present invention provides a method of preventing or treating cancer comprising administrating the adjuvant composition and at least one cancer-specific antigen. The cancer includes, but is not limited to, renal cell carcinoma, a melanoma, a chronic lymphocytic leukemia, a lung cancer, a cervical cancer, a stomach cancer, a thyroid cancer, a pancreatic cancer, a breast cancer, a prostate cancer, an ovarian cancer, a cholangioma, a liver cancer, a colon cancer, and a rectal cancer. The cancer-specific antigen includes, but is not limited to, gp100, MART-1 and MAGE-1, tyrosinase, CEA (cancer embryonic antigen), PSA (prostate specific antigen), HER2/neu, MAGE-1, MAGE-2, MAGE-3, NY-ESO-1, MUC-1, SART-1 or SART-3, TERT (telomerase reverse transcriptase) or a partial peptide derived from TERT, WT1 or a partial peptide derived from WT1, Survivin-2B or a partial peptide derived from Survivin-2B, gp75, MDM2, telomerase, alpha-1 fetoprotein, CA125, CA15-3, CA19-9, G250 and NY-ESO-1

Lastly, in another aspect, the present invention provides a vaccine kit comprising the adjuvant and technical instructions with information on the administration and dosage of the adjuvant.

BRIEF DESCRIPTION OF THE FIGURES

The preferred embodiments of the present invention is best understood with reference to the accompanying figures, wherein:

FIG. 3 presents a set of graphs showing the antibody isotypes induced by various different vaccine formulations with L-HBsAg in Alum, Pam3Cys-SKKKK alone, poly I:C alone, or both Pam3Cys-SKKKK and poly I:C as adjuvants. FIG. 3(a) illustrates the antibody titer of each isotype, FIG. 3(b) illustrates the ratio of IgG2a to IgG1 produced, and FIG. 3(c) illustrates the ratio of IgG2b to IgG1 produced.

FIG. 4 presents a graph showing the immunogenicity against Influenza virus HA antigen of the vaccines formulated with different adjuvants: Alum, Pam3Cys-SKKKK alone, poly I:C alone, or both Pam3Cys-SKKKK and poly I:C.

FIG. 5 presents a set of graphs showing the antibody isotypes induced by Influenza virus antigen formulated with different types of adjuvants: Alum, Pam3Cys-SKKKK alone, poly I:C alone, or both Pam3Cys-SKKKK and poly I:C.

FIG. 8(*a*) presents the antibody titer of each isotype, FIG. 8(*b*) presents the ratio of IgG2a to IgG1, and FIG. 8(*c*) illustrates the ratio of IgG2b to IgG1 produced.

FIG. 9 presents a graph showing the titer of antibody against preS antigen induced by various vaccine formulations with L-HBsAg and aluminum hydroxide (Alum), Pam3Cys-SKKKK alone, Pam3Cys-SR8 alone, FSL-1 alone, poly I:C alone, combination of Pam3Cys-SKKKK and poly I:C, combination of Pam3Cys-SR8 and poly I:C, or combination of FSL-1 and poly I:C as adjuvants. In this experiment pronounced effect of synergy between lipopeptide and poly I:C can be seen.

DETAILED DESCRIPTION OF THE INVENTION

Definition

Figure 1:
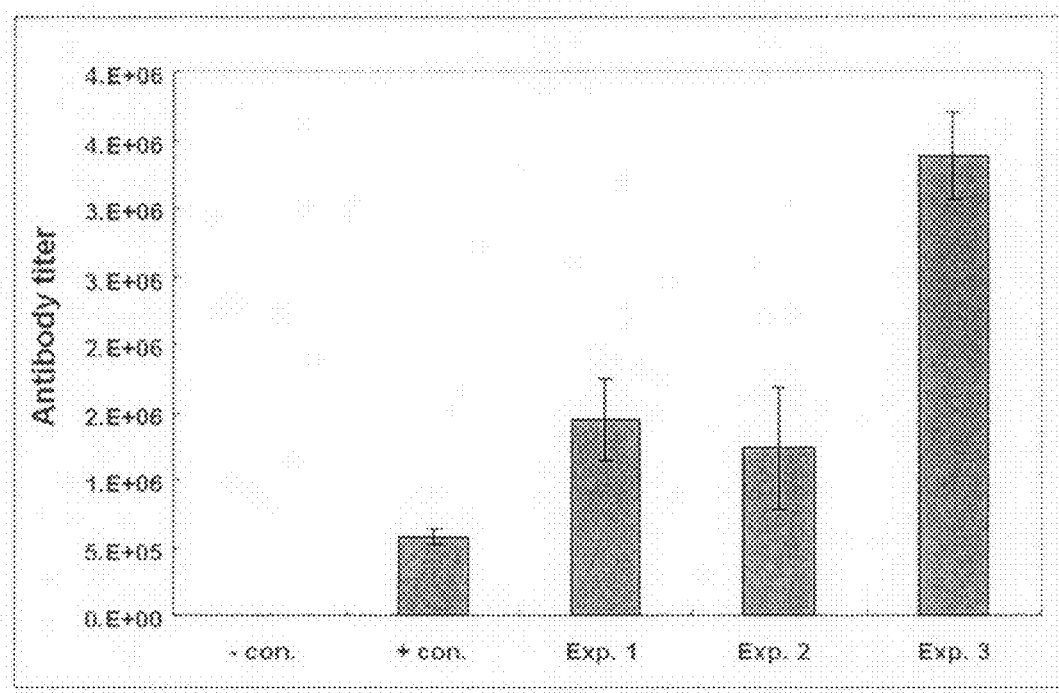
FIG. 1 presents a graph showing the titer of S-protein antibody elicited by various vaccine formulations containing L-HBsAg composed of L-protein (S-protein-preS2-preS1), M-protein (S-protein-preS2), and S-protein, in combination with the adjuvant aluminum hydroxide (Alum), Pam3Cys-SKKKK alone, poly I:C alone, or both Pam3Cys-SKKKK and poly I:C.

As used herein, the term "adjuvant" refers to a substance that increases or otherwise alters immune responses when mixed with an administered immunogenic. The adjuvant described in the present invention is the one that is able to induce a powerful antibody response as well as a cell-mediated immune response and that can switch an immunoglobulin isotype to produce IgG2a and IgG2b.

As used herein, the term "vaccine" refers to an antigenic suspension or solution usually comprising an infectious factor or a portion of an infectious factor, administered into the body to produce active immunity. The antigenic portion that constitutes a vaccine can be a microorganism (for example, virus or bacterium and the like) or a natural product purified from a microorganism, a synthetic or genetically engineered protein, peptide, polysaccharide or similar product. Examples of live vaccines include, but are not limited to, BCG, smallpox vaccination, polio, varicella, measles, rubella, mumps, rinderpest, NDV, Marek's disease and the like. Inactivated vaccines include, but are not limited to, pertussis, diphtheria (toxoid), tetanus (toxoid), influenza, Japanese encephalitis and the like.

As used herein, the term "poly(I:C)" or "poly I:C" refers to a double-stranded RNA comprising polyinosinic acid (pI) and polycytidylic acid (pc).

As used herein, the phrase "a powerful vaccine" refers to a vaccine formulation that can generate a large amount of high quality antigen specific antibody in reference to the most well known adjuvant aluminum hydroxide. In this regard, the generation of an appropriate, high quality antibody is a very important factor for producing a good preventive or an effective therapeutic vaccine. For example, different IgG isotypes play different roles in elimination of a tumor cells; IgG2a is the most effective one, compared with IgG1, IgG2b, or IgG3 (Nimmerjahn F & Ravetch J V, *Science* 310: 1510-1512, 2005). IgG2a and IgG2b, known to be the most effective in inducing antiviral immunity (Coutelier J P et al. *J Exp Med* 165:64-69, 1987; Markine-Gorianoff D & Coutelier J P, *J of Virol* 76:432-435, 2002), are generated by cytokines produced by Th1 cells, which also induce cell mediated immune response. Therefore, the induction of Th1 cell response is a good indication for the generation of an appropriate, high quality antibody. The most widely utilized adjuvant, Alum, induces Th 2 type immune response, and induced antibody is mainly IgG1.

Thus, the powerful vaccine composition of the present invention is judged by the amount of an antigen specific antibody generated and high ratios of IgG2a/IgG1 and IgG2b/IgG1 compared to widely utilized Alum adjuvant containing vaccine.

As used herein, the term "antigen" refers to a substance that induces a specific immune response when presented to immune cells of an organism. An antigen may comprise a single immunogenic epitope, or a multiplicity of immunogenic epitopes recognized by a B-cell receptor such as an antibody on the membrane of the B cell, or a T-cell receptor. A molecule may act as both an antigen and an adjuvant (e.g., cholera toxin).

As used herein, the term "parasite antigen" means a molecule derived from a parasite which is capable of inducing humoral response in a host. The parasite antigen can be a surface glyco-protein or a carbohydrate molecule thereof or a lipid molecule.

As used herein, the term "cancer-specific antigen" refers to a protein or an immunologically active fragment thereof which is differentially expressed in cancerous tissues rather than normal tissues.

As used herein, the term "administer" or "administrate" as used herein means that the vaccine and the like of the present invention or a pharmaceutical composition containing the same is given to a host to be treated, alone or in combination with another therapeutic agent. The combination can be administered, for example, simultaneously in a mixture, separately but simultaneously or concurrently; or sequentially. This includes presentation wherein the combined drugs are administered together in a therapeutic mixture, and also includes procedures wherein the combined drugs are administered separately but simultaneously (for example, to the same individual via separate mucosae).

It is noted that, as used in the present application including this specification and the claims, the singular forms "a," "an" and "the" include plural references unless the context clearly dictates otherwise.

Further, it is noted that, as used in the present application including this specification and the claims, the range of values, such as concentration ranges, percentage ranges, or ratio ranges, is understood such that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the present invention, subject to any specifically excluded limit in the stated range. Where the stated range includes one or both of the limits, ranges excluding either or both of those included limits are also included in the present invention.

Further, for purposes of better understanding the present teachings and in no way limiting the scope of the teachings, unless otherwise indicated, all numbers expressing quantities, percentages or proportions, and other numerical values used in the specification and the claims, are to be understood as being modified in all instances by the term "about." Accordingly, unless indicated to the contrary, the numerical parameters set forth in the following specification and the claims are approximations that may vary depending upon the desired properties sought to be obtained. At the very least, each numerical parameter should at least be construed in light of the number of reported significant digits and by applying ordinary rounding techniques.

Unless defined otherwise, all other technical and scientific terms used herein have the same meaning as commonly understood to one of ordinary skill in the art to which the present invention pertains.

Preferred Embodiment

In a preferred embodiment of the present invention, a synergistic adjuvant for a vaccine composition is provided. In particular, the synergistic adjuvant comprises one or more lipopeptides and poly I:C (polyinosinic:polycytidylic acid) and can stimulate immune responses in a synergistic way, instead of giving an additive effect by each adjuvant component. For this, in a preferred embodiment of the present invention, Pam3Cys-SKKKK, a lipopeptide, and poly I:C were mixed using a conventional method known to the art. A simple mixture forms, not requiring a covalent bond between the lipopeptide and poly I:C.

The lipopeptide as used in the present invention is composed of fatty acids linked to glycerol and amino acids. The lipopeptide contains one or more fatty acids in each molecule. The lipopeptide can be a lipoprotein composed of a part of or a whole molecule originated from gram positive or gram negative bacteria or mycoplasma. The fatty acid and the amino acid can be synthesized with chemical modifications. The lipopeptide in the preferred embodiment is exemplified by, but is not limited to, Pam3Cys-SKKKK as shown in the following Formula I. The molecular structure of the lipopeptide in Formula I is N-palmitoyl-S-[2,3-bis(palmitoyloxy)-(2RS)-propyl]-[R]-cystein-SKKKK). Other lipopeptides that can be used in the present invention include PHC-SKKKK, Ole2 PamCys-SKKKK, Pam2Cys-SKKKK, PamCys(Pam)-SKKKK, Ole2Cys-SKKKK, Myr2Cys-SKKKK, PamDhc-SKKKK, PamCSKKKK and Dhc-SKKKK.

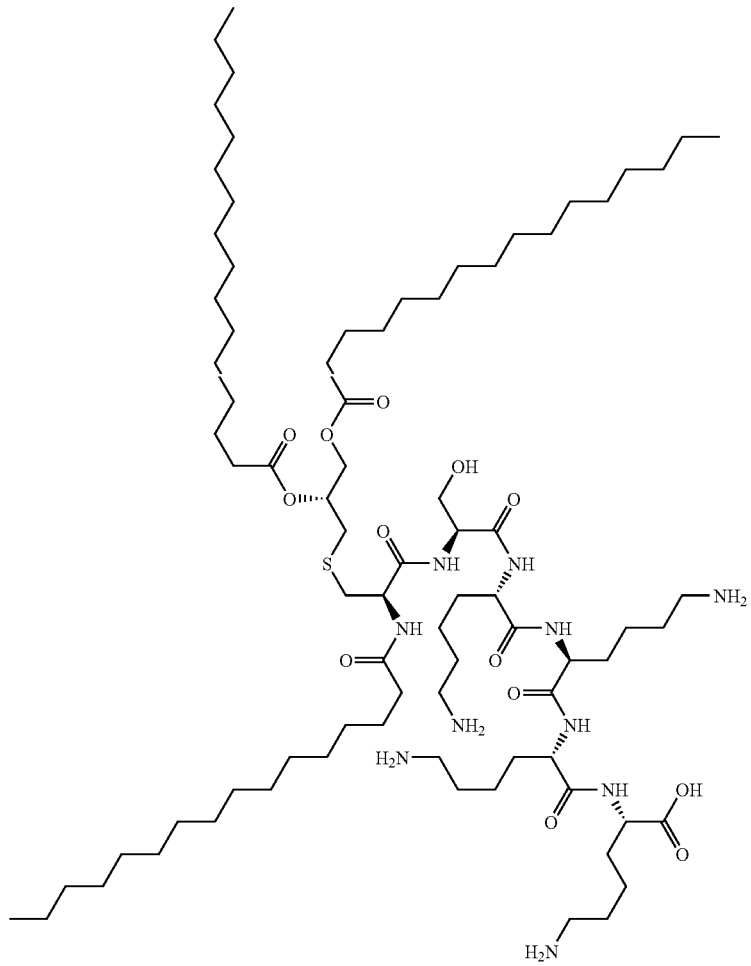

Poly I:C (polyinosinic:polycytidylic acid) as used in the present invention is a synthetic double stranded RNA. The length of poly I:C is preferably 50-2000 bp, more preferably being 100-500 bp.

The present invention in another aspect provides a vaccine composition comprising the synergistic adjuvant and at least one antigen. The mixture of a lipopeptide and poly I:C was used as an adjuvant to produce a vaccine composition in combination with L-HBsAg, an influenza antigen, or with a mixture of HBsAg S-protein and PreS as an antigen. In a preferred embodiment of the present invention, the vaccine composition comprises a mixture of Pam3Cys-SKKKK and poly I:C. The vaccine composition was found to enhance antigen-specific antibody production in a significant level, as compared to the most frequently used conventional adjuvant, aluminum hydroxide (see FIGS. 1, 2, 4, 6 and 7, and Tables 1, 2 and 3).

When the mixture of Pam3Cys-SKKKK and poly I:C is used, the vaccine composition exhibited a synergistic effect in stimulating immune responses, that is, the titer of pre S antibody induced by the vaccine composition containing the mixture as an adjuvant was several times higher than the combined level of the antibody titer induced by the individual components of the mixture. This is well illustrated in FIG. 2, in which the antibody titer of pre S antibody was assessed for the mixture and each individual component as an adjuvant. This synergistic effect is less significant for S-protein antibody induction (see FIG. 1), which is because the amount of the antigen used in all experiments was a saturating amount, instead of the right amount that can show adjuvant dependency. Pre S content in L-protein is less than 10% of the total (5 mg).

When a vaccine is formulated using aluminum hydroxide, which is known to induce Th2 immune response, IgG1 antibody is the predominant IgG isotype present. Whereas, when a vaccine is formulated using the mixture comprising Pam3Cys-SKKKK and poly I:C, IgG2a and IgG2b are the predominant IgG isotypes produced. Therefore, the ratios of IgG2a/IgG1 and IgG2b/IgG1 are higher in the mixture of Pam3Cys-SKKKK and poly I:C, as compare to the ratio obtained with the conventional adjuvant, aluminum hydroxide (see FIGS. 3, 5 and 8, and Tables 1, 2 and 3). This increase of IgG2a and IgG2b, which is known to be very effective in defense against viral infection and cancer, suggests that the quality of immune response has improved with the new adjuvant according to the present invention. Further, these findings indicate that the adjuvant comprising a lipopeptide and poly I:C according to the present invention can be effectively used for the development of powerful therapeutic and prophylactic vaccine formulations.

In a preferred embodiment of the present invention, a vaccine composition prepared using the adjuvant of the present invention was proved to synergistically increase the antigen specific antibody production, as well as changing the quality

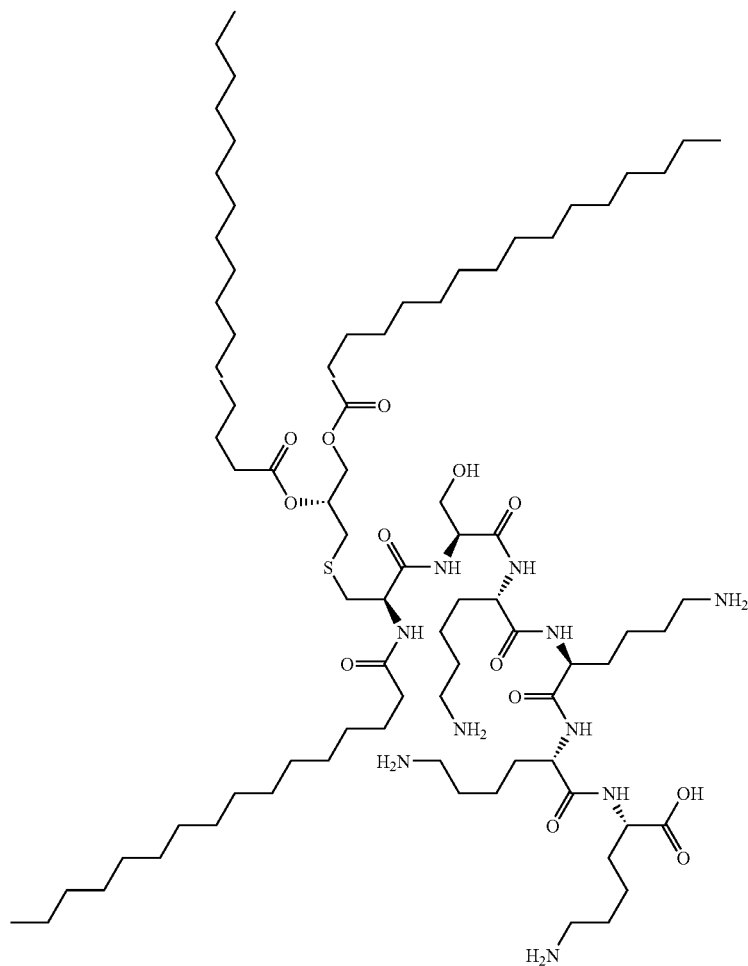

of immune response by inducing mostly IgG2a and IgG2b (see FIGS. 1-8 and Tables 1-3). Therefore, an adjuvant composition containing the adjuvant components according to the present invention can be effectively used to increase immunogenicity of an antigen, thereby improving the efficacy of the vaccine containing the adjuvant and the antigen in combination.

The antigen that can be used in the present invention can be any material or substance that can induce immune responses by the immune system of an animal or human. It can be full length or a fragment. It can be a synthetic material, a purified subunit or a whole microbe or a mixture. A purified antigen is preferred. The antigen may include, but is not limited to, a recombinant protein, a peptide from hepatitis virus or viral protein from influenza virus, a polysaccharide, a glycoprotein, a lipopolysaccharide, a DNA molecule, a cancer cell, a live virus or a hapten molecule, etc. The protein of a pathogen may include, but is not limited to, influenza virus antigen (HA: haemagglutinin or neuraminidase antigen), *Bordetella pertussis* antigen, pertussis toxin, filamentous haemagglutinin, human papilloma virus (HPV) antigen, *Helicobacter pylori* antigen (capsular polysaccharides of serogroup A, B, C, Y and W-135), tetanus toxoid, diphtheria antigen (diphtheria toxoid), pneumococcal antigen (*Streptococcus pnemoniae* type 3 capsular polysaccharides), tuberculosis antigen, human immunodeficiency virus (HIV) antigen (GP-120, GP-160), cholera antigen (cholera toxin B subunit), staphylococcal antigen (staphylococcal enterotoxin B), shigella antigen (shigella polysaccharides), vesicular stomatitis virus antigen (vesicular stomatitis virus glycoprotein), cytomegalovirus (CMV) antigen, hepatitis antigen [hepatitis A(HAV), B(HBV), C(HCV), D(HDV) and G(HGV): L-HBsAg, S-HBsAg, M-HBsAg, pre S], respiratory synctytial virus (RSV) antigen, herpes simplex antigen and combinations thereof (ex: diphtheria, pertussis and tetanus; DPT).

The vaccine composition of the present invention may additionally include one or more active ingredient(s) having the same or a similar effect with them. In this regard, the present invention further provides a pharmaceutical composition comprising the adjuvant according to the present invention and at least one active ingredient. Any active ingredient known to those skilled in the art may be used. In some embodiments, an active ingredient may be selected from peptides, proteins, nucleic acids, low molecular weight organic or inorganic compounds having a molecular weight less than 5000, sugars, antigens, antibodies, and therapeutic agents. The pharmaceutical compositions of the present invention may further comprise another adjuvant selected from the group consisting of aluminum hydroxide, complete Freund's adjuvant, incomplete Freund's adjuvant, stabilizing cationic peptides, polypeptides, protamine, nucleoline, spermine, spermidine, cationic polysaccharides, chitosan, TDM, MDP, muramyl dipeptide, alum solution, and pluronics. The pharmaceutical compositions of the invention may be used for any purpose known to those skilled in the art. In some embodiments, a pharmaceutical composition according to the invention may be a vaccine.

The vaccine composition can also include, in addition to the above-mentioned active ingredients, one or more pharmaceutically acceptable carriers to aid the administration. The pharmaceutically acceptable carrier can be selected or be prepared by mixing one or more ingredients selected from the group consisting of saline, sterilized water, Ringer's solution, buffered saline, dextrose solution, maltodextrose solution, glycerol and ethanol. Other general additives such as anti-oxidative agents, buffer solutions, bacteriostatic agents, etc., can be added. In order to prepare injectable solutions such as aqueous solutions, suspensions and emulsions, diluents, dispersing agents, surfactants, binders and lubricants can be additionally added. The vaccine composition of the present invention can further be prepared in suitable forms depending on the diseases to be treated or prevented or the ingredients included in the composition by following the preparation method presented in Remington's Pharmaceutical Science (the newest edition, Mack Publishing Company, Easton, Pa.).

The vaccine composition of the present invention can be administered parenterally by various routes such as subcutaneous injection, intravenous injection, intramuscular injection and intrathoracic injection. To prepare the vaccine composition as a formulation for parenteral administration, the vaccine composition is mixed with a stabilizer or a buffering agent to produce a solution or suspension, which is then formulated to ampoules, syringes, or vials in single or multiple doses. The vaccine composition of the present invention can be formulated to a sterilized aqueous solution or suspension for injection or a freeze-dried form. The freeze-dried vaccine composition is stored typically at 4° C. and can be reconstituted with a stabilizer that may contain an additive such as saline and/or HEPES. Further, the vaccine composition of the present invention may be formulated as an oil emulsion and supplied in a tightly stoppered ampoule, vial, syringe, atomizer or the like, or in a thermally sealed ampoule.

The dosage of the vaccine composition of the present invention can be determined in consideration of various factors including, but is not limited to, the administration method and frequency, the disease to be treated or prevented, the severity of the disease, the history of the disease, the therapeutic agent to be co-treated, and the age, height, weight, health condition or physical condition of the subject to be treated. Generally, the dose of the present vaccine composition is increased according to the weight increase of a patient to be treated. In a preferred embodiment of the present invention, the vaccine composition can be administered parenterally, by intraperitoneal injection, hypodermic injection, intravenous injection or intramuscular injection. The vaccine composition can be administered at a dose sufficient to stimulate immune responses in a subject. For example, the vaccine can be administered to a human once or several times, each time at the dose of 1-250 µg, and more preferably 10-100 µg.

The present invention provides a method for generating an appropriate, high quality antibody by administering the vaccine composition according to the present invention to a subject in need thereof. In a preferred embodiment of the present invention, the vaccine composition prepared according to the present invention increases the antigen specific antibody production and the IgG2a and IgG2b production (see FIGS. 1-10 and Tables 1-4). Therefore, the vaccine composition of the present invention can be effectively used for the mass-production of an appropriate, high quality antibody for which the stimulation of immunogenicity of an antigen is required.

The present invention provides a method for enhancing Th1 immune response by administering the vaccine composition according to the present invention to a subject in need thereof. In a preferred embodiment of the present invention, the vaccine composition prepared by using the adjuvant of the present invention increased IgG2a and IgG2b production (see FIGS. 3, 5, 8 and 10, and Tables 1, 2, 3 and 4). Therefore, the vaccine composition of the present invention can be effectively used for enhancing Th1 immune response to improve immunogenicity of an antigen.

The present invention provides a method for treating a viral or parasitic infection comprising administrating the adjuvant of claim 1 and at least one viral antigen or parasite antigen to a subject in need thereof. In a preferred embodiment of the present invention, the pharmaceutical composition or the vaccine composition prepared with the adjuvant of the present invention increases the antigen specific antibody production and the IgG2a and IgG2b production (see FIGS. 1-10 and Tables 1-4). IgG2a and IgG2b are known to be effective in defending viral infection and cellular infection of parasites. Therefore, the pharmaceutical or vaccine composition comprising the adjuvant according to the present invention and at least one viral or parasite antigen can be effectively used to treat the viral or parasite infection.

In a preferred embodiment of the present invention, the viral antigen is influenza virus antigen (HA: haemagglutinin or neuraminidase antigen), human papilloma virus (HPV) antigen, human immunodeficiency virus (HIV) antigen (GP-120, GP-160), vesicular stomatitis virus antigen (vesicular stomatitis virus glycoprotein), cytomegalovirus (CMV) antigen, hepatitis antigen [hepatitis A(HAV), B(HBV), C(HCV), D(HDV) and G(HGV): L-HBsAg, S-HBsAg, M-HBsAg, pre S], respiratory synctytial virus (RSV) antigen or herpes simplex virus antigen.

In preferred embodiment of the present invention, the parasite includes, but is not limited to, protozoa, nematoda, trematoda or cestoda. The protozoa are preferably a rhizopoda, a mastigophora, a ciliate or a sporozoa, but are not limited thereto. The rhizopoda includes, but is not limited to, *Entamoeba histoytica* and *Entamoeba coli*. The mastigophora includes, but is not limited to, *Giardia lamblia*, *Trichomonas vaginalis*, *Trichomonas hominis* and *Haemoflagellates*. The cilliate includes *Balantidium coli*. The sporozoa is preferably a *Plasmodium* sp. including *P. vivax* and *P. falciparum*, a *Toxoplasma gondii*, *Pneumocystis carinii*, *Isospora hominis*, and *Cryptosporidium* sp. including *C. parvum* and *C. muris*.

The nematoda is preferably a whipworm, a hookworm, a pinworm, an ascarid or a filariodea, but is not limited thereto. The whipworm is preferably *Trichuris trichiura* or *Trichocephalus trichiuris*, but is not limited thereto. However, any other whipworms infecting animals such as dogs, cats and pigs may be included. The hookworm is preferably *Ancylostoma duodenale* or *Necator americanus*, but is not limited thereto. The pinworm is preferably *Enterobius vermicularis* or *Enterobius gregorii*. The ascarid is preferably *A. suum* which typically infects pigs or *A. lumbricoides* which infects humans. The filariodea is preferrably *Wuchereria bancroffi*, *Onchocerca volvulus*, *Loa loa* or *Dirofilaria immitis*.

The trematoda is preferably Digenea, but is not limited thereto. The Digenea includes Schistosome or non-Schistosome. The schistosome includes *Schistosoma mansoni*, *Schistosoma haematobium*, *Schistosoma japonicun* and *Schistosoma intercalatum*, but is not limited thereto. The non-Schistosome includes *Fasciolopsis buski*, *Heterophyes heterophyes*, *Metagonimus yokogawaii*, *Gastrodiscoides hominis*, *Clonorchis sinensis*, *Fasciola hepatica* and *Paragonimus westermani*, but is not limited thereto.

The cestoda is preferably Taeniidae or Diphyllobothriidae, but is not limited thereto. Taeniidae includes *Taenia solium* and *Taenia saginata*. The Diphyllobothriidae includes *Diphyllobothrium* sp. such as *Diphyllobothrium latum* *Diphyllobothrium dendriticum*, *D. nihonkaiense*, *D. pacificum*, *D. cordatum*, *D. ursi*, *D. lanceolatum*, *D. dalliae*, and *D. yonagoensis*.

In a preferred embodiment of the present invention, the parasite antigen may be a molecule derived from a parasite that can induce a humoral immune response in a host. It can be a surface glyco-protein or a carbohydrate molecule thereof or a lipid molecule. Non-limiting examples of the parasite antigen known in the art include a helminth parasite antigen characterized by (i) in native form being an integral membrane protein; (ii) having a native localization in the parasite gut; (iii) being capable of binding to a thiol affinity medium; and (iv) being recognized by sera from immunized animal hosts (WO 95/26402 A1), a helminth parasite antigen possessing aminopeptidase-like activity (WO 9512671 A1), a noninfectious soluble fraction of a *Toxoplasma gondii* infected cell culture lysate (U.S. Pat. No. 6,399,077), an isolated and purified antigen conferring protective immunity against a non-obligate blood feeding helminth and which is characterized by possessing aminopeptidase M-like activity (U.S. Pat. No. 6,413,521), a novel Fasciclin Related Adhesive Protein (FRAP) from Plasmodium and related parasites (US 20070087012 A1), a protective metazoan parasite antigen capable of binding to pepstatin (WO 9402169 A1), parasite antigens of *Dirofilaria immitis* (U.S. Pat. No. 4,656,251) and circulating parasite antigens of *Dirofilaria immitis* (U.S. Pat. No. 4,839,275).

The present invention provides a method for preventing or treating cancer comprising administrating the adjuvant described herein and at least one cancer-specific antigen to a subject in need thereof.

The cancer is preferably a renal cell carcinoma, a melanoma, a chronic lymphocytic leukemia, a lung cancer, a cervical cancer, a stomach cancer, a thyroid cancer, a pancreatic cancer, a breast cancer, a prostate cancer, an ovarian cancer, a cholangioma, a liver cancer, a colon cancer, or a rectal cancer, but is not limited thereto.

The cancer-specific antigen that may be used in the present invention includes, but is not limited to, gp100, MART-1 and MAGE-1, which are well known to be specific for menanoma, tyrosinase, CEA (cancer embryonic antigen), PSA (prostate specific antigen), HER2/neu, MAGE-1, MAGE-2, MAGE-3, NY-ESO-1, MUC-1, SART-1 or SART-3, TERT (telomerase reverse transcriptase) or partial peptides derived from TERT, WT1 or partial peptides derived from WT1, Survivin-2B or partial peptides derived from Survivin-2B, gp75, MDM2, telomerase, alpha-1 fetoprotein, CA125, CA15-3, CA19-9, G250 and NY-ESO-1 (See WO 2006/078059 and WO 2007/065957). Additional cancer-associated antigen CAA and a method for identifying CAA is disclosed by Miller (*Drug Discovery Today*, 8: 31-38, 2003), by Kawakami and Rosenberg (*Immunol. Res.* 16:313, 2003) and by Slingluff et al. (*Curr. Opin. Immunol.*, 6:733, 1994).

In addition, the present invention provides the use of an adjuvant comprising one or more lipopeptide(s) and poly I:C in the manufacture of an immunological therapeutic agent for treating cancer for which a strong cellular immune response is required. In a preferred embodiment of the present invention, the immunological therapeutic agent prepared by using the adjuvant of the present invention increased antigen-specific antibody production and IgG2a and IgG2b production (see FIGS. 1-10 and Tables 1-4). IgG2a and IgG2b are known to be very effective in anticancer immune response. Therefore, the immunological therapeutic agent composition containing the adjuvant for the vaccine of the present invention and an appropriate cancer-specific antigen can be effectively used as a preventive or therapeutic agent for preventing or treating cancer. The immunological agent for preventing or treating cancer can be administered parenterally by hypodermic injection, intravenous injection or intramuscular injection. To prepare the vaccine composition as a formulation for parenteral administration, the vaccine composition of the present invention is formulated as an oil emulsion, which is then stored as ampoules, syringes, or vials. The effective dosage can be determined according to absorption rate, inactivation rate, age, gender, health condition of a patient, and severity of disease, etc.

In another aspect, the present invention provides a vaccine kit for preventing and/or treating an infectious disease or a cancer. This kit is provided with the adjuvant described herein and technical instructions with information on the administration and dosage of the adjuvant. This kit can be sold as a pharmaceutical in a package. The instruction sheet bears a statement of approval from regulatory authorities such as the Food and Drug Administration and a statement indicating how to use the kit. The methods of preparing and -administering the vaccine are the same as those herein described above.

EXAMPLES

The following examples illustrates the present formulations, but they are not intended to limit the scope of the present claims. It should be appreciated that a person of ordinary skill in the art may modify and/or improve the following examples within the spirit and scope of the present invention.

Example 1

Stimulation of Immunogenicity of Hepatitis B Virus (HBV) Antigen

Vaccines were prepared with hepatitis B virus antigen and various adjuvants including aluminum hydroxide (Alum; Brenntag Biosector, Germany), Pam3Cys-SKKKK (lipopeptide) (EMC microcollections GmbH, Germany) alone, poly I:C (Sigma, USA) alone, or the mixture of both Pam3Cys-SKKKK and poly I:C. The antibody titer induced by each of the vaccine formulations was compared.

1-1. Preparation of Vaccines and Administration

Vaccines were prepared by mixing hepatitis B virus whole surface antigen (L-HBsAg; Korean Patent No: 10-0836745) and said various adjuvants. The formulated vaccines were administered to mice. L-HBsAg consists of S-protein (small protein without pre S1 and pre S2), M-protein (medium protein with pre S2 only), and L-protein (large protein with both preS1 and preS2).

In particular, as shown in Table 1, 20 μg of Pam3Cys-SKKKK, poly I:C and a mixture of Pam3Cys-SKKKK and poly I:C were respectively mixed with 0.5 μg of L-HBsAg to give vaccines in oil emulsion form. The antibody titer induced by the vaccine formulations was compared. As a positive control, the same amount of the antigen was formulated with aluminum hydroxide and as a negative control, PBS buffer solution without antigen and adjuvant was administered. Vaccines were injected intra-muscularly into 6 week old C57BL/6 female mice three times by two week intervals.

TABLE 1

|  | Negative control | Positive control | Experimental group 1 | Experimental group 2 | Experimental group 3 |
|---|---|---|---|---|---|
| Adjuvant | — | Aluminum hydroxide | Pam3Cys-SKKKK | Poly I:C | Pam3Cys-SKKKK + poly I:C |
| HBsAg antibody titer | — | $5.7 \times 10^5$ | $1.4 \times 10^6$ | $1.2 \times 10^6$ | $3.4 \times 10^6$ |
| PreS antibody titer | — | $7.1 \times 10^4$ | $6.2 \times 10^5$ | $6.5 \times 10^5$ | $5.1 \times 10^6$ |
| IgG2a/IgG1 (%) | — | 3.6 | 8.9 | 9.1 | 39.4 |
| IgG2b/IgG1 (%) | — | 9.5 | 153.9 | 66.4 | 374.8 |

1-2. Analysis of Immune Response

1-2-1. Antibody Titer Against HBsAg (S-Protein)

Serum was collected respectively before the vaccine administration (i.e., pre-immune serum) and 2 weeks after the third vaccine administration, and the generated antigen specific antibody was analyzed by the ELISA method to determine the antibody titer.

Particularly, a 96-well microplate was coated with recombinant S-protein (Dobeel Corp., Korea) at the concentration of 100 ng/well and blocked by adding 1% BSA (Bovine Serum Albumin) for one hour. After the microplate was washed, appropriately diluted serum was added to each well and the microplate was incubated at 37° C. for 2 hours. Then, anti mouse goat IgG-HRP (Horse Radish Peroxidase; Sigma, USA) as a secondary antibody was added to each well and the microplate was incubated at 37° C. for one hour. At the end of incubation, the microplate was washed extensively with PBST (PBS with Tween 20) and TMB (3,3',5,5'-tetramethyl benzidine) peroxidase substrate solution (KPL, USA) was added, followed by incubation at room temperature for 20 minutes. Then, $OD_{450}$ was measured with the ELISA reader. Antibody titer was determined as the inverse value of antibody final dilution to give an OD reading that is three times higher than the OD of the negative control.

As shown in Table 1 and FIG. 1, Pam3Cys-SKKKK or poly I:C was more effective than aluminum hydroxide in inducing higher antibody titer against S-protein of HBV envelop protein. Especially, when the mixture of Pam3Cys-SKKKK and poly I:C was used, the induced antibody titer was slightly higher than the combined value of the antibody titer induced by each component of the mixture, which indicates the synergistic effect by the two components. The synergistic effect of the combined use of Pam3Cys-SKKKK and poly I:C is more pronounced in the induction of PreS antibody. This can be due to the amount of antigen used, since the amount of preS in L-HBsAg preparation is less than 10% of the total. The 0.5 ug of antigen is near the saturating amount for immune response in mice (data not presented).

1-2-2. Antibody Titer Against preS

Antibody titer was determined by the same method as described in Example 1-2-1 except that preS antigen (Dobeel Corp., Korea) was used as an antibody capturing antigen.

Figure 2:
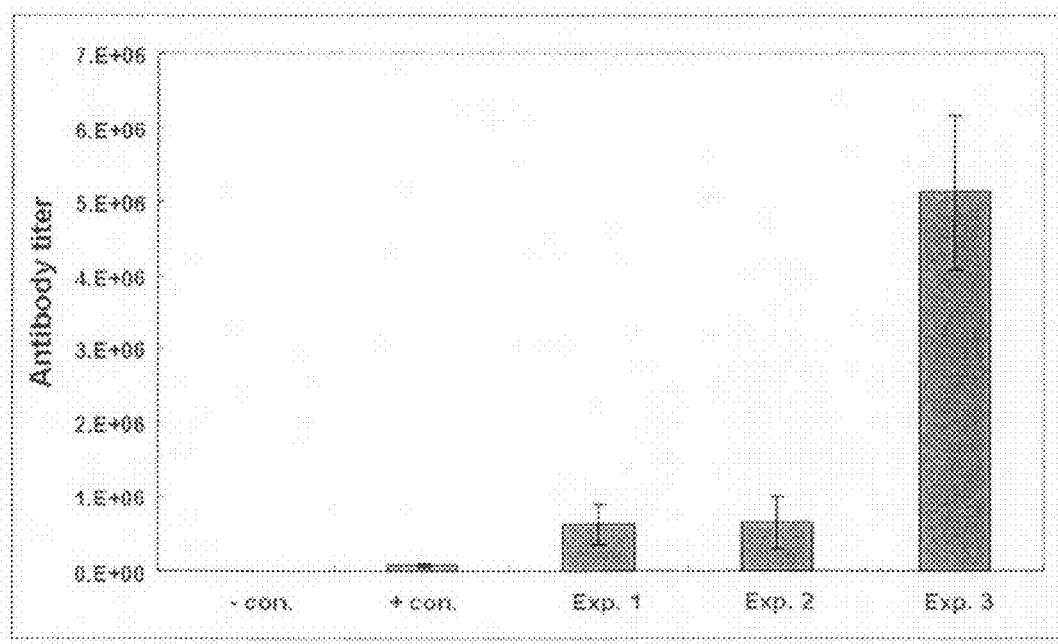
FIG. 2 presents a graph showing the titer of antibody against preS antigen induced by various vaccine formulations with L-HBsAg and Alum, Pam3Cys-SKKKK alone, poly I:C alone, or both Pam3Cys-SKKKK and poly I:C as adjuvants. This graph demonstrates the significant synergistic effect by the mixture of Pam3Cys-SKKKK and poly I:C.

As shown in Table 1 and FIG. 2, the adjuvant mixture containing both Pam3Cys-SKKKK and poly I:C was more effective, inducing higher antibody titer against preS. Induction of pre S antibody by the adjuvant mixture was synergistic, inducing more than 4 times of preS antibody as compared to the added value of the two preS antibody titers induced by Pam3Cys-SKKKK alone and poly I:C alone, respectively.

In particular, as shown in Table 2, 20 μg of Pam3Cys-SKKKK alone, poly I:C alone, the mixture of Pam3Cys-SKKK and poly I:C, and aluminum hydroxide were respectively mixed with 1.8 μg of the split vaccine antigen to give various different vaccine formulations in an oil emulsion form. These different formulations were given by intramuscular injection to 5 week old C57BL/6 female mice two times at three week intervals. The negative control was injected with only PBS, while the positive control was injected with the antigen alone without any adjuvant. Each group contains 6 mice.

TABLE 2

|  | Negative control | Positive control 1 | Positive control 2 | Experimental group 1 | Experimental group 2 | Experimental group 3 |
| --- | --- | --- | --- | --- | --- | --- |
| Adjuvant | — | — | Aluminum hydroxide | Pam3Cys-SKKKK | Poly I:C | Pam3Cys-SKKKK + poly I:C |
| HA antibody titer | — | $2.1 \times 10^5$ | $9.3 \times 10^5$ | $6.8 \times 10^5$ | $8.6 \times 10^5$ | $3.0 \times 10^6$ |
| IgG2a/IgG1 (%) | — | 8.85 | 6.09 | 7.59 | 6.17 | 31.67 |

1-2-3. Isotypes of Induced HBsAg Specific Antibody

Antibody titer was determined by the same method as described in Example 1-2-1 except that IgG1, IgG2a and IgG2b (mouse monoclonal antibody isotyping reagents; Sigma, USA) were used as a secondary antibody. IgG2a/IgG1 and IgG2b/IgG1 ratios were calculated by using the obtained antibody titer.

As shown in FIG. 3a, isotypes IgG2a and IgG2b were much higher in value with the adjuvant mixture as compared to the values obtained with aluminum hydroxide. Especially, the induction of IgG2b was more than 20 times the value obtained with aluminum hydroxide. When the adjuvant mixture comprising Pam3Cys-SKKKK and poly I:C was used, the IgG2a/IgG1 ratio was about 10 times higher than for aluminum hydroxide. Especially, the production of IgG2b was significantly higher, and IgG2b/IgG1 ratio was much higher than IgG2a/IgG1 (FIG. 3(b) and FIG. 3(c)).

Example 2

Stimulation of Immunogenicity of Influenza Virus Antigen

Influenza virus antigen was formulated as vaccines using aluminum hydroxide, Pam3Cys-SKKKK alone, poly I:C alone, or the mixture of Pam3Cys-SKKKK and poly I:C, as adjuvants, and then the antibody titer induced was determined using influenza virus antigen as the capturing antigen as for the HBsAg antibody assay.

2-1. Formulation of Influenza Virus Antigen and Administration

Different formulations were prepared by mixing recombinant split vaccine antigen (Korea Vaccine Co., Ltd, Korea) and said adjuvants, then the formulations were administered to mice. The antigen was prepared by infecting the allantoic sac of a developing egg with influenza virus strains A/New Caledonia/20/99(H1N1), a/Wisconsin/67/2005(H3N2) and B/Malaysia/2506/2004, culturing, purifying and inactivating thereof.

2-2. Analysis of Immune Response

Serum was collected from each mouse respectively before the vaccine administration and 2 weeks after the second vaccine administration, and the generated antigen specific antibody was analyzed by the ELISA method to determine the antibody titer.

2-2-1. Determination of HA Antibody Titer

Antibody titer was determined by the same manner as described in Example 1-2-1 except that HA antigen (Korea Vaccine Co., Ltd, Korea) was used as an antibody capturing antigen.

As shown in Table 2 and FIG. 4, the mixture of Pam3Cys-SKKKK and poly I:C was more effective in inducing higher antibody titer against HA (synergistic effect) than each component of the mixture or aluminum hydroxide.

2-2-2. Isotypes of Induced HA Specific Antibody

Antibody titer was determined by the same way as described in Example 2-2-1 except that IgG1 and IgG2a were used as secondary antibodies for isotype determination. IgG2a/IgG1 and IgG2b/IgG1 ratios were also calculated by using the obtained antibody titer.

Figures 5A, 5B:
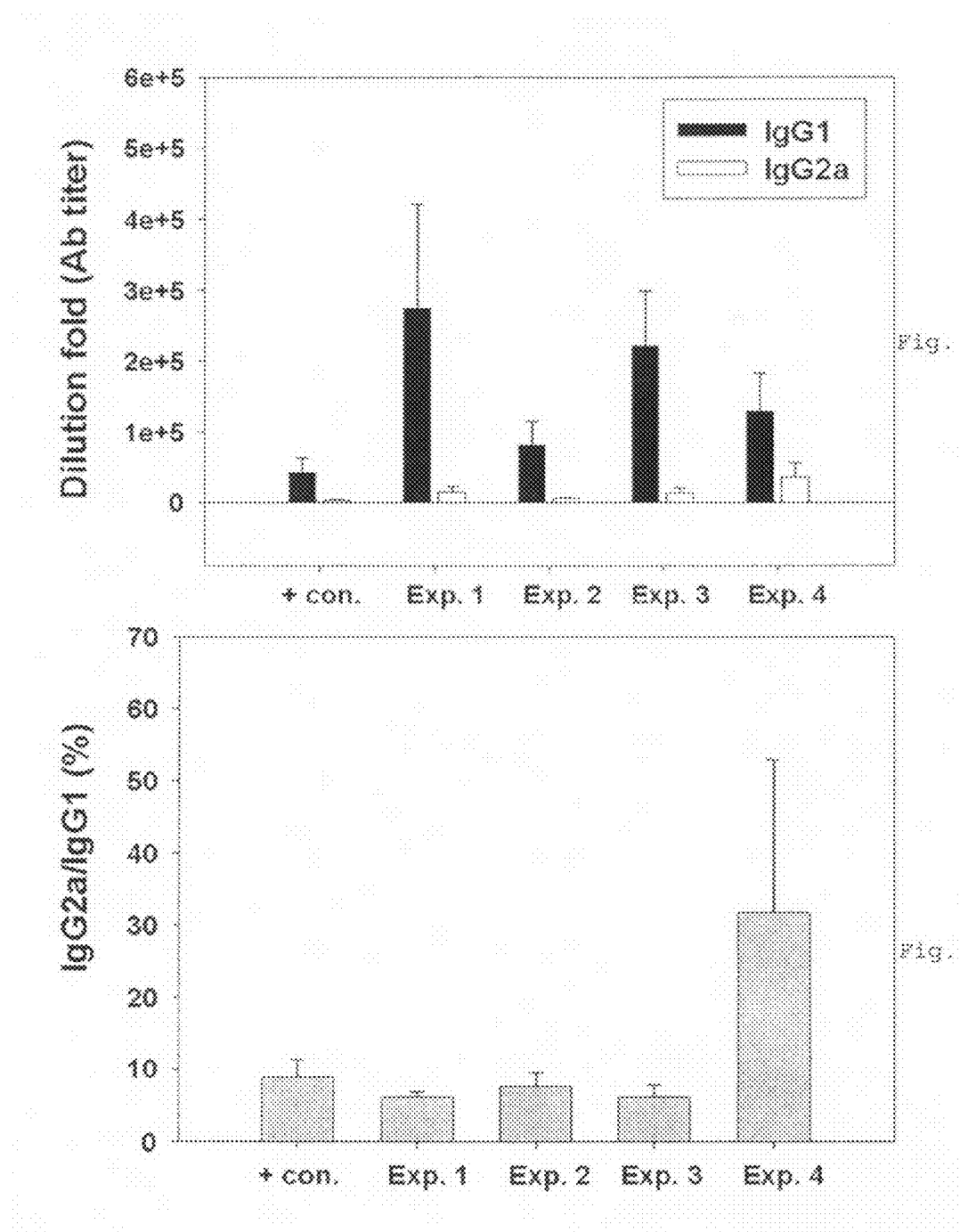
FIG. 5(a) presents the antibody titer of each isotype.
FIG. 5(b) presents the ratio of IgG2a to IgG1 produced.

FIG. 5(a) shows the antibody titers of isotypes IgG1 and IgG2a. Isotype ratios were also calculated using the antibody titers. The IgG2a/IgG1 value was significantly higher (FIG. 5(b)) with the adjuvant mixture as compared to the value obtained with each component of the mixture or Aluminum hydroxide.

Example 3

Preparation of a Powerful Vaccine Using Recombinant HBsAg (S-Protein from *Hansenula polymorpha*) and Recombinant preS Protein (from *Saccharomyces cerevisiae*)

Various vaccine formulations were prepared with recombinant HBsAg and recombinant preS protein by using aluminum hydroxide or the mixture of Pam3Cys-SKKKK and poly I:C as adjuvants, and immune responses induced were compared.

3-1. Preparation of Vaccines and Administration Thereof

Vaccines were prepared by mixing recombinant HBsAg (Dobeel Corp., Korea), recombinant preS protein (Dobeel Corp., Korea) and said adjuvants, and they were administered by intramuscular injection to mice. The recombinant HBsAg contained only S-protein without preS antigen and the recombinant preS protein prepared as a particle type by conjugating them to colloidal gold, were used as antigens.

Particularly, a mixture containing 20 μg of each Pam3Cys-SKKKK and poly I:C was used as an adjuvant, with 0.5 μg of recombinant S-protein and 5 μg of preS protein to give a vaccine in an oil emulsion form. Each test vaccine contained 0.5 μg of the recombinant S-protein and 5 μg of the preS per dose, which was then given by intramuscular injection to 5 week old C57BL/6 female mice three times at two week intervals.

The negative control group was injected with PBS only. The positive control group was injected with the mixture comprising aluminum hydroxide, S-protein, and colloidal gold conjugated recombinant preS antigen. Experimental group 1 was injected with a vaccine prepared by mixing emulsified S-protein, Pam3Cys-SKKKK and poly I:C and colloidal gold conjugated recombinant preS antigen. Experimental group 2 was injected with a vaccine prepared by emulsification of all components together, including S-protein, colloidal gold conjugated recombinant preS antigen and the mixture of Pam3Cys-SKKKK and poly I:C.

3-2. Analysis of Immune Responses

Serum samples were collected respectively before the vaccine administration and 2 weeks after the third vaccine administration, and the generated antigen specific antibody was analyzed by the ELISA method and expressed with the antibody titer.

3-2-1. Antibody Titer Against S-Protein

Antibody titer against S-protein was determined by the same way as described in Example 1-2-1.

Figure 6:
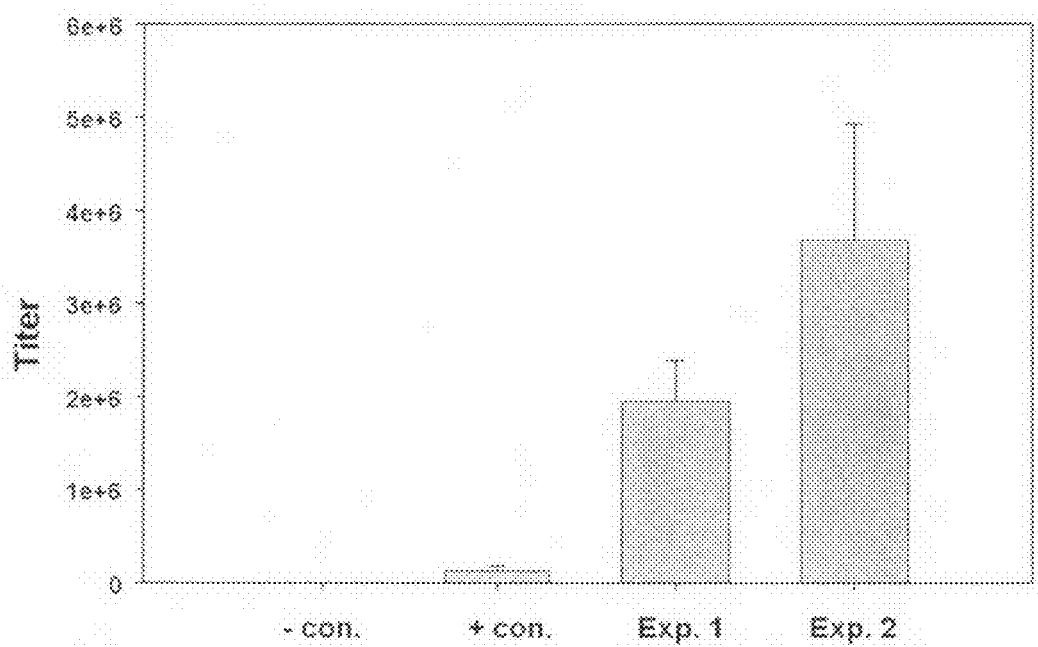
FIG. 6 presents a graph showing the immunogenicity of the vaccines against HBsAg antigen (S-protein) from *Hansenula polymorpha* and preS from *Saccharomyces cereviciae* formulated in different adjuvants: Alum, Pam3Cys-SKKKK alone, poly I:C alone, or both Pam3Cys-SKKKK and poly I:C.

As shown in Table 3 and FIG. 6, the adjuvant mixture of Pam3Cys-SKKKK and poly I:C induced more than 10 times higher antibody titer against S-protein than that of aluminum hydroxide. Particularly, the vaccine prepared by emulsifying all components together induced higher antibody titer than the vaccine prepared by emulsifying S-protein with the said adjuvant first, and adding the conjugated preS.

TABLE 3

|  | Negative control | Positive control 1 | Experimental group 1 | Experimental group 2 |
|---|---|---|---|---|
| HBsAg antibody titer | — | $1.3 \times 10^5$ | $1.9 \times 10^6$ | $3.6 \times 10^6$ |
| PreS antibody titer | — | $4.6 \times 10^5$ | $1.2 \times 10^6$ | $2.0 \times 10^6$ |
| IgG2a/IgG1 (%) | — | 35 | 83 | 162 |
| IgG2b/IgG1 (%) | — | 6 | 110 | 324 |

3-2-2. Pre S Antibody Titer

PreS antibody titer was determined by the same manner as described in Example 1-2-2.

Figure 7:
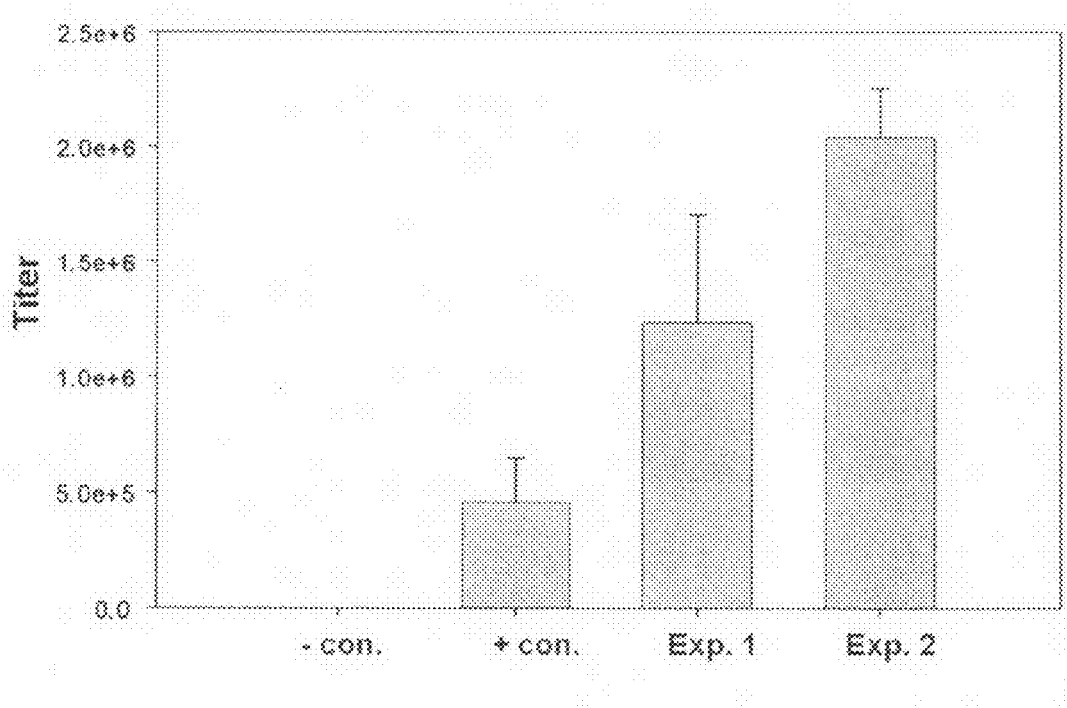
FIG. 7 presents a graph showing the immunogenicity of the vaccines against preS antigen formulated with Hansenula S-protein and preS from yeast in different adjuvants: Alum, Pam3Cys-SKKKK alone, poly I:C alone, or both Pam3Cys-SKKKK and poly I:C.

As shown in Table 3 and FIG. 7, the mixture of Pam3Cys-SKKKK and poly I:C as an adjuvant induced higher antibody titer against preS as compared to aluminum hydroxide. Particularly, the vaccine prepared by emulsifying all components together—including HBsAg and preS antigen with the said adjuvant—induced pre S antibody most efficiently, inducing more than 3 times of the antibody by aluminum hydroxide.

3-2-3. Isotypes of Induced HBsAg Specific Antibody

Isotype antibody titer was determined by the same method as described in Example 1-2-3. IgG2a/IgG1 and IgG2b/IgG1 ratios were calculated from the obtained antibody titer.

Figure 8A:
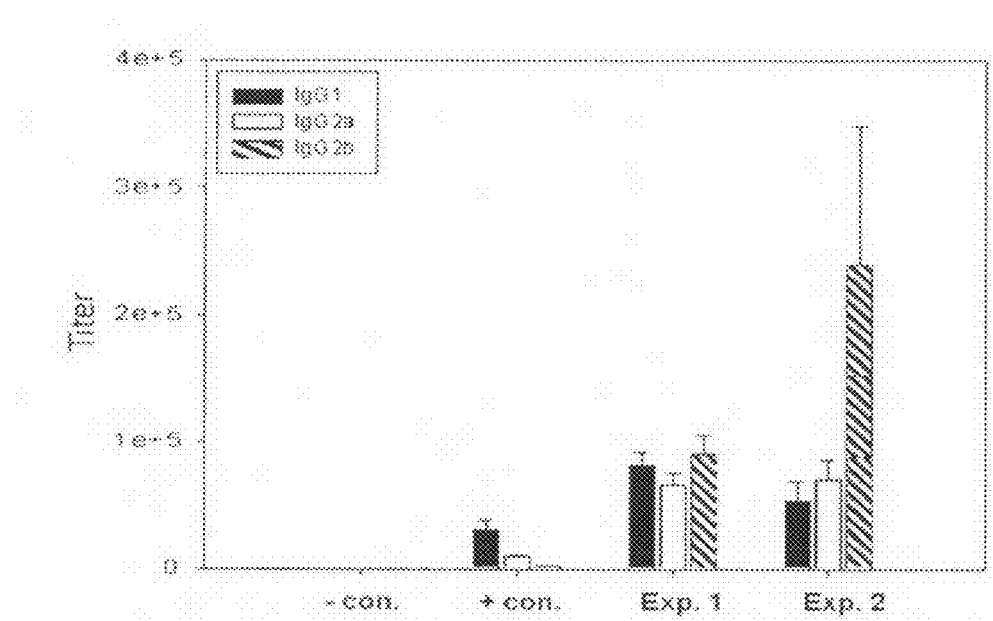
FIG. 8 presents a set of graphs showing the antibody isotypes induced by vaccines formulated with HBsAg (S-protein) from Hansenula and preS from yeast in different adjuvants: Alum, Pam3Cys-SKKKK alone, poly I:C alone or both Pam3Cys-SKKKK.
Figure 8B:
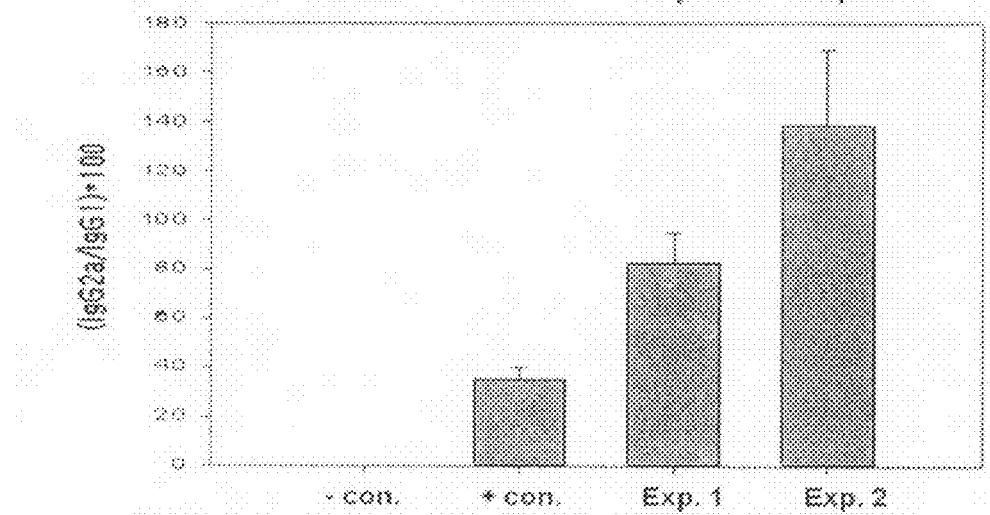
Figure 8C:
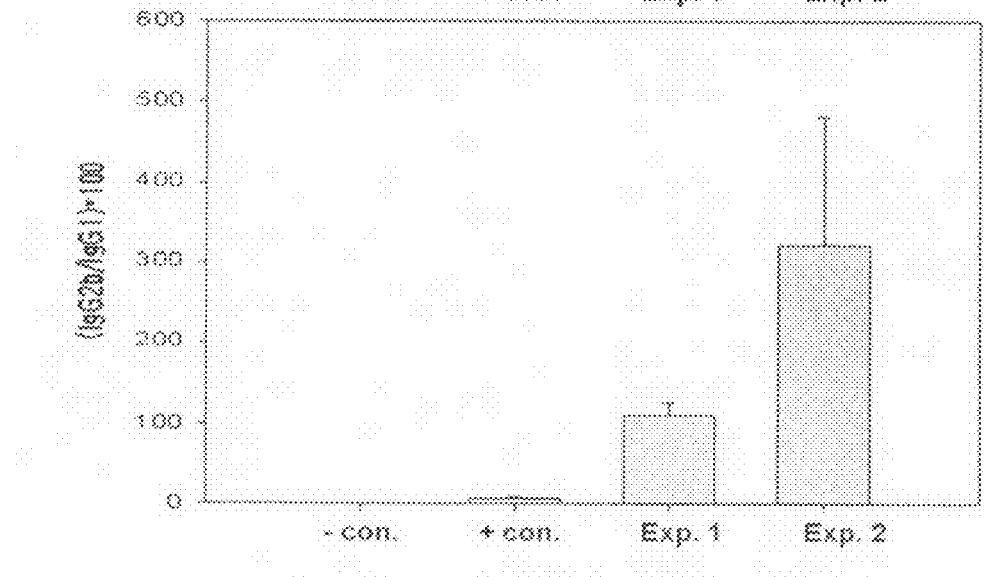

As shown in FIG. 8a, antibody titers of isotypes IgG1, IgG2a and IgG2b were obtained. Isotype ratios were also calculated using the antibody titers. When the adjuvant mixture of Pam3Cys-SKKKK and poly I:C was used, IgG2a/IgG1 and IgG2b/IgG1 ratios were higher than that in the aluminum hydroxide. In particular, the vaccine, prepared by mixing HBsAg and preS antigen with the said adjuvant and emulsifying together, was confirmed more effective than the vaccine prepared by mixing preS antigen with emulsified HBsAg and the said adjuvant (FIGS. 8b and 8c).

Example 4

Adjuvant Composition Using Various Lipopeptides

To test the synergistic adjuvant effect of various lipopeptides with poly I:C, Pam3Cys-SKKKK, Pam3Cys-SR8 and FSL-1 (Fibroblast-stimulating lipopeptide) were used as a lipopeptide and they were formulated with poly I:C and hepatitis B virus antigen.

4-1. Preparation of Vaccines and Administration

Vaccines were prepared by mixing hepatitis B virus whole surface antigen that was preadsorbed on aluminum hydroxide and said adjuvant components, and they were administered to mice. In the course of the experiments, it was noticed that the aluminum hydroxide adsorbed antigen is more stable, and the aluminum hydroxide has no noticeable effect on the adjuvant effect of the lipopeptide and poly I:C mixture.

Particularly, as shown in Table 4, 0.5 μg of L-HBsAg absorbed to aluminum hydroxide was formulated with 20 μg of each of the lipopeptides or poly I:C (experimental group 1-4). Also the same amount of antigen was formulated with the mixture of lipopeptide and poly I:C (experimental group 5-7).

Vaccines were injected intramuscularly into 6 week old C57BL/6 female mice three times at two week intervals. The negative control was administered only with PBS without the vaccine and the antigen, while the positive control was administered with the antigen formulated with aluminum hydroxide.

TABLE 4

| | Adjuvant | HBsAg antibody titer | preS antibody titer | IgG2a/IgG1 (%) | IgG2b/IgG1 (%) |
|---|---|---|---|---|---|
| Negative control | — | — | — | — | — |
| Positive control | Aluminum hydroxide | $5.9 \times 10^5$ | $1.6 \times 10^5$ | 3.6 | 21.6 |
| Experimental group 1 | Pam3Cys-SKKKK | $6.5 \times 10^5$ | $1.3 \times 10^5$ | 17.4 | 159.4 |
| Experimental group 2 | Pam3Cys-SR8 | $4.8 \times 10^5$ | $1.8 \times 10^2$ | 34.3 | 550.03 |
| Experimental group 3 | FSL-1 | $4.4 \times 10^5$ | $1.4 \times 10^5$ | 9.3 | 122.5 |
| Experimental group 4 | Poly I:C | $6.3 \times 10^5$ | $2.3 \times 10^5$ | 8.04 | 89.05 |
| Experimental group 5 | Pam3Cys-SKKKK + Poly I:C | $3.0 \times 10^6$ | $1.4 \times 10^6$ | 63.7 | 805.6 |
| Experimental group 6 | Pam3Cys-SR8 + Poly I:C | $1.7 \times 10^6$ | $1.5 \times 10^6$ | 50.4 | 306.2 |
| Experimental group 7 | FSL-1 + Poly I:C | $9.8 \times 10^5$ | $6.4 \times 10^5$ | 23.9 | 510.5 |

4-2. Analysis of Immune Response

Serum was collected from each mouse before the vaccine administration and 2 weeks after the last vaccine administration, and the generated antigen specific antibody was analyzed by the ELISA method to determine the antibody titer.

4-2-1. Antibody Titer Against HBsAg (S-Protein)

Antibody titer was determined by the same method as described in Example 1-2-1.

As shown in Table 4 and FIG. 9, when the mixture of the lipopeptide (such as Pam3Cys-SKKKK and Pam3Cys-SR8) and poly I:C was used, the antibody titer induced was slightly higher than the combined value of individually induced antibody titer, indicating a synergistic effect by the two components.

4-2-2. Antibody Titer Against preS

Antibody titer was determined by the same way as described in Example 1-2-1 except that preS antigen (Dobeel Corp., Korea) was used as an antibody capturing antigen.

Figure 10:
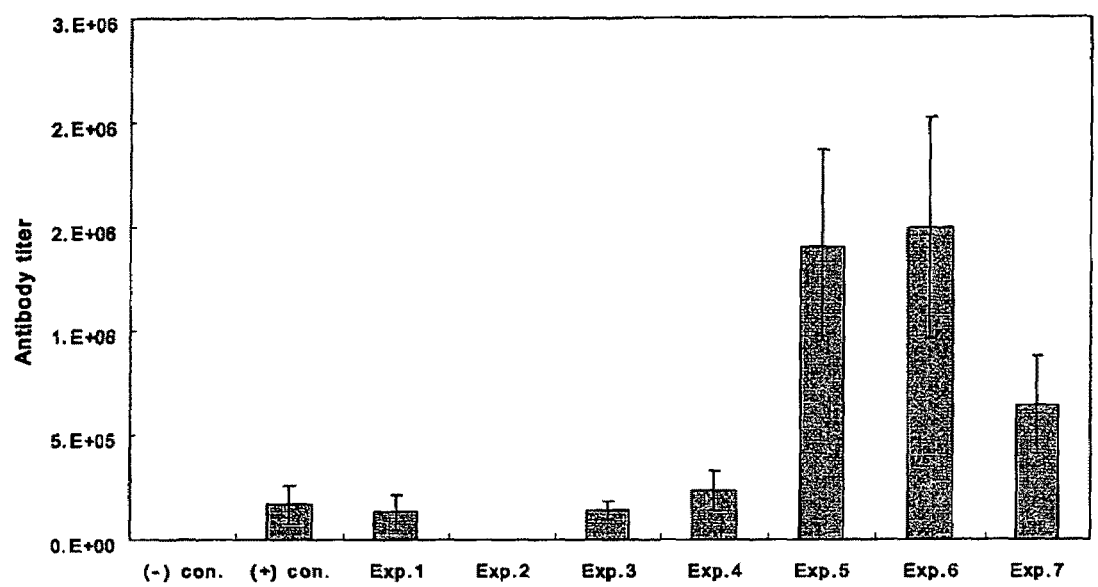
FIG. 10 presents a set of graphs showing the antibody isotypes induced by various different vaccine formulations with L-HBsAg in aluminum hydroxide (Alum), Pam3Cys-SKKKK alone, Pam3Cys-SR8 alone, FSL-1 alone, poly I:C alone, a combination of Pam3Cys-SKKKK and poly I:C, a combination of Pam3Cys-SR8 and poly I:C, or a combination of FSL-1 and poly I:C as adjuvants.

As shown in Table 4 and FIG. 10, the adjuvant mixture containing one of the lipopeptides and poly I:C was more effective in inducing higher antibody titer against preS. The synergistic effect by the combination of the lipopeptides, other than Pam3Cys-SKKKK, and poly I:C is also more dramatic for pre S antibody generation as seen before with Pam3Cys-SKKKK and poly I:C in the example 1-2-2.

4-2-3. Isotypes of Induced HBsAg Specific Antibody

Antibody titer was determined by the same manner as described in Example 1-2-1 except that IgG1, IgG2a and IgG2b were used as secondary antibodies. The IgG2a/IgG1 and IgG2b/IgG1 ratios were also calculated by using the obtained antibody titer.

Figure 11A:
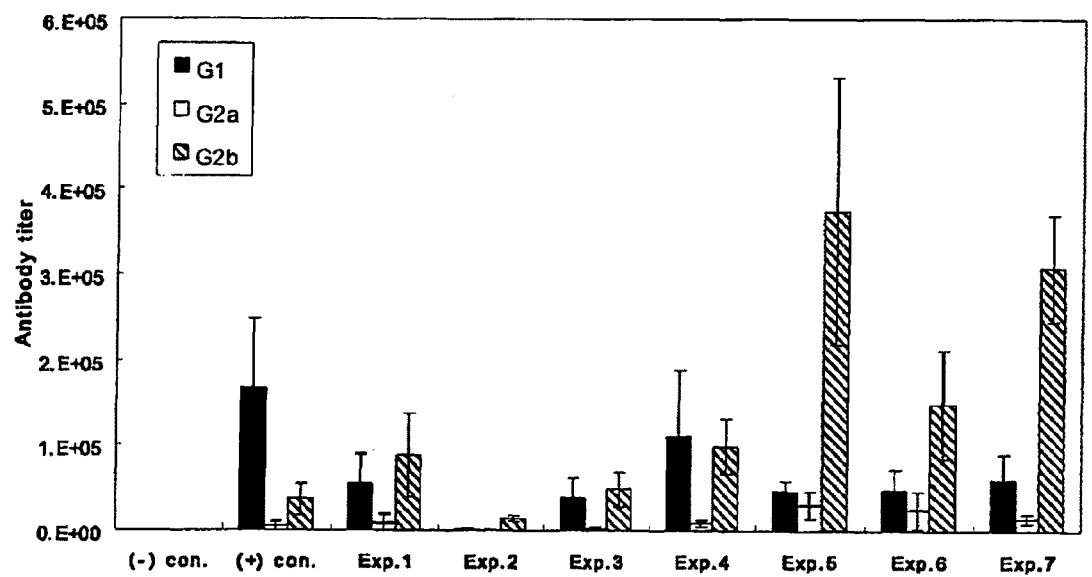
FIG. 11(*a*) presents the antibody titer of each isotype, FIG. 11(*b*) presents the ratio of IgG2a to IgG1, and FIG. 11(*c*) presents the ratio of IgG2b to IgG1.
Figure 11B:
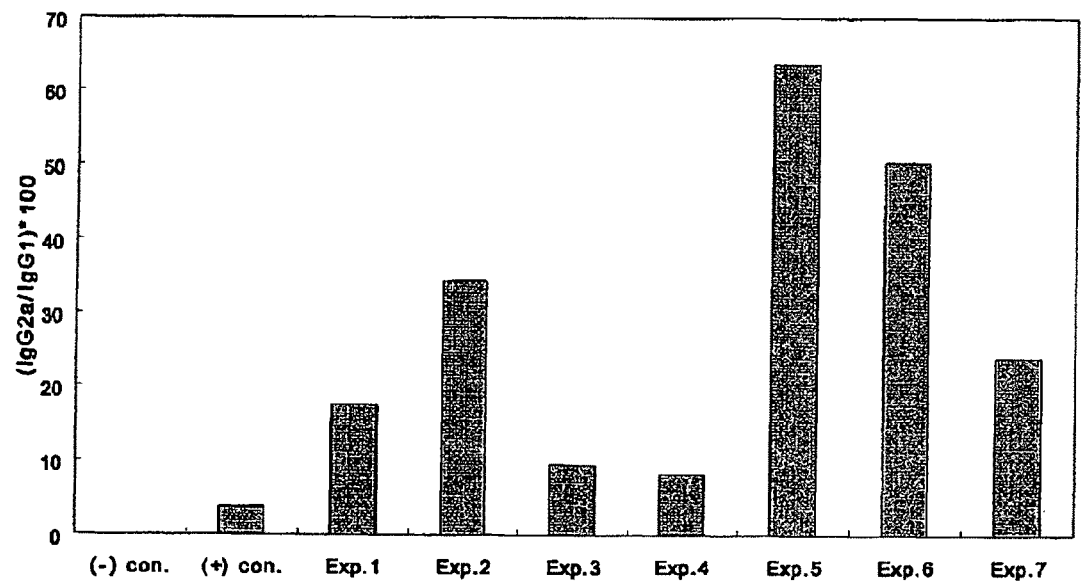
Figure 11C:
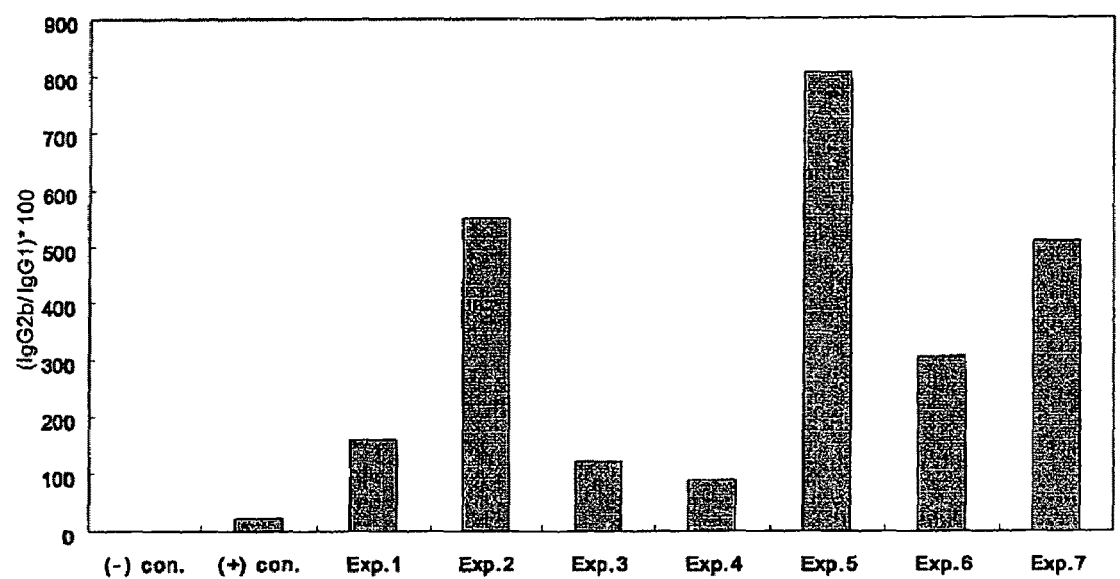

As shown in FIG. 11*a*, antibody titers of isotypes IgG2a and IgG2b were much higher in the case that the combination of the lipopeptide and poly I:C was used as an adjuvant, as compared to the value induced with aluminum hydroxide as an adjuvant. Consequently the IgG2a/IgG1 and IgG2b/IgG1 ratios were also higher when the adjuvant mixture was used (FIG. 11(*b*)(*c*)). The synergistic effects were similar when the Pam3Cys-SKKKK, Pam3Cys-SR8 or FLS-1 was used as the lipopeptide component. Specifically, the combination of Pam3Cys-SKKKK and poly I:C was the most effective.

A person of ordinary skill in the art will appreciate that the conceptions and specific embodiments disclosed in the foregoing description may be readily utilized as a basis for modifying or designing other embodiments for carrying out the same purposes of the present invention. A person of ordinary skill in the art will also appreciate that such equivalent embodiments do not depart from the spirit and scope of the invention as set forth in the appended claims.

What is claimed is:

1. An adjuvant comprising one or more lipopeptide(s) selected from the group consisting of Pam3Cys-SKKKK and Pam3Cys-SR8, and poly I:C(polyinosinic:polycytidylic acid), wherein the lipopeptide and poly I:C synergistically stimulate induction of adaptive immune responses.

2. The adjuvant according to claim 1, wherein the poly I:C is about 50-2,000 bp in length.

3. A vaccine composition comprising the adjuvant of claim 1 and at least one antigen.

4. The vaccine composition according to claim 3, wherein the antigen is selected as a single or multiple component(s) from the group consisting of a protein of a pathogen, a recombinant protein, a peptide, a hapten, a polysaccharide, a glycoprotein, a lipopolysaccharide, a DNA molecule (polynucleotide), a cancer cell, a micro-organism, and mixtures thereof.

5. The vaccine composition according to claim 3, wherein the antigen is selected from the group consisting of L-HBsAg, influenza HA, S-protein, and preS.

6. The vaccine composition according to claim 3, wherein the vaccine is capable of efficiently inducing cell mediated immune response and producing antigen-specific antibodies.

7. The vaccine composition according to claim 6, wherein the antibodies comprise IgG1, IgG2a and IgG2b type antibodies.

8. A pharmaceutical composition comprising the adjuvant of claim 1 and at least one active ingredient.

9. The pharmaceutical composition according to claim 8, further comprising at least one ingredient selected from the group consisting of pharmaceutically acceptable carriers, pharmaceutically acceptable additives and adjuvants.

10. A method for generating an antibody comprising administrating the vaccine composition of claim 3 to a subject in need thereof.

11. The method according to claim 10, wherein the method facilitates mass-production of an antibody.

12. A method for enhancing Th1 immune response comprising administrating the vaccine composition of claim 3 to a subject in need thereof.

13. A method for inducing an immune response against a viral or parasitic infection comprising administrating the adjuvant of claim 1 and at least one viral antigen or parasite antigen to a subject in need thereof.

14. The method according to claim 13, wherein the viral antigen is selected from the group consisting of influenza virus antigen (HA: haemagglutinin or neuraminidase antigen), human papilloma virus (HPV) antigen, human immunodeficiency virus (HIV) antigen (GP-120, GP-160), vesicular stomatitis virus antigen (vesicular stomatitis virus glycoprotein), cytomegalovirus (CMV) antigen, hepatitis antigen [hepatitis A(HAV), B(HBV), C(HCV), D(HDV) and G(HGV): L-HBsAg, S-HBsAg, M-HBsAg, pre S], respiratory syncytial virus (RSV) antigen and herpes simplex virus antigen.

15. The method according to claim 13, wherein the parasite is selected from the group consisting of protozoa, nematoda, trematoda and cestoda.

16. A method for inducing an immune response against cancer comprising administrating the adjuvant of claim 1 and at least one cancer-specific antigen to a subject in need thereof.

17. The method according to claim 16, wherein the cancer is selected from the group consisting of renal cell carcinoma, a melanoma, a chronic lymphocytic leukemia, a lung cancer, a cervical cancer, a stomach cancer, a thyroid cancer, a pancreatic cancer, a breast cancer, a prostate cancer, an ovarian cancer, a cholangioma, a liver cancer, a colon cancer, and a rectal cancer.

18. The method according to claim 16, wherein the cancer-specific antigen is selected from the group consisting of gp100, MART-1 and MAGE-1, tyrosinase, CEA (cancer embryonic antigen), PSA (prostate specific antigen), HER2/neu, MAGE-1, MAGE-2, MAGE-3, NY-ESO-1, MUC-1, SART-1 or SART-3, TERT (telomerase reverse transcriptase) or a partial peptide derived from TERT, WT1 or a partial peptide derived from WT1, Survivin-2B or a partial peptide derived from Survivin-2B, gp75, MDM2, telomerase, alpha-1 fetoprotein, CA125, CA15-3, CA19-9, G250 and NY-ESO-1.

19. A vaccine kit comprising the adjuvant of claim 1 and technical instructions with information on the administration and dosage of the adjuvant.

* * * * *